(12) United States Patent
Singer et al.

(10) Patent No.: US 11,058,664 B2
(45) Date of Patent: Jul. 13, 2021

(54) IN VITRO AND XENOGRAFT ANTI-TUMOR ACTIVITY OF A HALOGENATED-XANTHENE AGAINST REFRACTORY PEDIATRIC SOLID TUMORS

(71) Applicants: Provectus Pharmatech, Inc., Knoxville, TN (US); UTI Limited Partnership, Calgary (CA)

(72) Inventors: Jamie Singer, Knoxville, TN (US); Eric A. Wachter, Oak Ridge, TN (US); Satbir Thakur, Calgary (CA); Lucy Swift, Calgary (CA); Chunfen Zhang, Calgary (CA); Mohit Jain, Calgary (CA); Aru Narendran, Calgary (CA)

(73) Assignees: Provectus Pharmatech, Inc., Knoxville, TN (US); UTI Limited Partnership, Calgary (CA)

( * ) Notice: Subject to any disclaimer, the term of this patent is extended or adjusted under 35 U.S.C. 154(b) by 0 days.

(21) Appl. No.: 16/412,872

(22) Filed: May 15, 2019

(65) Prior Publication Data
US 2019/0350893 A1    Nov. 21, 2019

Related U.S. Application Data

(60) Provisional application No. 62/672,373, filed on May 16, 2018.

(51) Int. Cl.
| | | |
|---|---|---|
| A61K 31/343 | (2006.01) | |
| C07K 16/28 | (2006.01) | |
| A61K 45/06 | (2006.01) | |

(52) U.S. Cl.
CPC ........ A61K 31/343 (2013.01); C07K 16/2818 (2013.01); C07K 16/2827 (2013.01); A61K 45/06 (2013.01)

(58) Field of Classification Search
CPC .. A61K 31/343; A61K 45/06; C07K 16/2818; C07K 16/2827
See application file for complete search history.

(56) References Cited

U.S. PATENT DOCUMENTS

| | | | |
|---|---|---|---|
| 5,998,597 A | 12/1999 | Fisher et al. | |
| 6,331,286 B1 | 12/2001 | Dees et al. | |
| 6,493,570 B1 | 12/2002 | Dees et al. | |
| 7,390,668 B2 | 6/2008 | Dees et al. | |
| 7,648,695 B2 | 1/2010 | Dees et al. | |
| 8,974,363 B2 | 3/2015 | Dees et al. | |
| 2003/0133940 A1 | 7/2003 | Dees et al. | |
| 2015/0290165 A1* | 10/2015 | Eagle | A61P 35/04 424/85.2 |
| 2017/0173079 A1 | 6/2017 | Singer et al. | |
| 2018/0055926 A1 | 3/2018 | Eagle et al. | |

FOREIGN PATENT DOCUMENTS

WO   2017009843 A2   1/2017

OTHER PUBLICATIONS

MerckManuals, Jul. 2019 (Year: 2019).*
ACS, https://www.cancer.org/cancer/cancer-in-children/types-of-childhood-cancers.html, 2019 (Year: 2019).*
Savelli et al. https://www.healthychildren.org/English/health-issues/conditions/cancer/Pages/Childhood-Cancer.aspx, 2019 (Year: 2019).*
Dana-Farber Cancer Institute, 2020 (http://www.danafarberbostonchildrens.org/conditions/solid-tumors.aspx) (Year: 2020).*
Bellanti et al. Eur J Clin Pharmacol (2011) 67 (Suppl 1):S87-S107 (Year: 2011).*
Hurley, https://www.healio.com/news/hematology-oncology/20200709/despite-treatment-advances-much-to-improve-upon-in-highrisk-neuroblastoma, 2020 (Year: 2020).*
Kline et al. (J of Pediatric Nursing, vol. 18, No. 2, Apr. 2003) (Year: 2003).*
Maker et al. (J Clin Cell Immunol. Aug. 6, 2015 (4), 2015). (Year: 2015).*
Biospace (https://www.biospace.com/article/releases/provectus-announces-agreement-with-poetic-pediatric-oncology-experimental-therapeutics-nvestigatorsconsortium-to-study-potential-of-pv-10-for-pedi/) (Year: 2016).*
Clinical Leader (https://www.clinicalleader.com/doc/provectus-elicitation-study-patient-perceiv (Year: 2017).*
Kopp, Oncoimmunology, 2016, 5, 4, p. 1-8 (Year: 2016).*
Chen, X. et al, "Pediatric Solid Tumor Genomics and Developmental Pliancy," Oncogene, vol. 34, 2015, pp. 5207-5215; doi:10.1038/onc.2014.474.
Cheung, N-K, et al, "Neuroblastoma: Developmental Biology, Cancer Genomics, and Immunotherapy," Nat. Rev. Cancer, vol. 13, No. 6, Jun. 2013, pp. 397-411; doi:10.1038/nrc3526.
Qin, J. et al, "Colon Cancer Cell Treatment with Rose Bengal Generates a Protective Immune Response via Immunogenic Cell Death," Cell Death and Disease, 2017, 8:e2584; doi:10.1038/cddis.2016.473.

(Continued)

*Primary Examiner* — Umamaheswari Ramachandran
(74) *Attorney, Agent, or Firm* — Husch Blackwell LLP

(57) ABSTRACT

A method of treating a pediatric cancerous solid tumor in a mammalian subject is disclosed that comprises intralesionally administering an amount of a halogenated xanthene or a pharmaceutically acceptable salt thereof, preferably Rose Bengal disodium, that elicits ablation of tumor cells of the administered tumor. Another contemplated method comprises the steps of intralesionally administering an amount of a halogenated xanthene or a pharmaceutically acceptable salt thereof, preferably Rose Bengal disodium, that elicits ablation of tumor cells of the administered tumor and systemically administering a tumor-inhibiting effective amount of a systemic anti-cancer medication that provides synergistic cytotoxicity with the halogenated xanthene. The two administrations can occur concurrently, or one prior to the other.

13 Claims, 12 Drawing Sheets

(56) References Cited

OTHER PUBLICATIONS

Toomey, P. et al, "Intralesional Injection of Rose Bengal Induces a Systemic Tumor-Specific Immune Response in Murine Models of Melanoma and Breast Cancer," PLOS One, vol. 8, issue 7, 2013; e68561.
Zamani, S. et al, "Rose Bengal Suppresses Gastric Cancer Cell Proliferation via Apoptosis and Inhibits Nitric Oxide Formation in Macrophages," Journal of Immunotoxicology, vol. 11, No. 4, 2014, pp. 367-375; doi:10.3109/1547691x.2013.853715.
Thompson, J.F. et al, "Phase 2 Study of Intralesional PV-10 in Refractory Metastatic Melanoma," Annals of Surgical Oncology, vol. 22, No. 7, 2015, pp. 2135-2142; doi:10.1245/s10434-014-4169-5.
Foote, M. et al, "Results of a Phase II, Open-Label, Non-Comparative Study of Intralesional PV-10 Followed by Radiotherapy for the Treatment of In-Transit or Matastatic Melanoma," Journal of Surgical Oncology; 2017; 9999:1-7; doi:10.1002/jso.24580.
Liu, H. et al,. "Intralesional Rose Bengal in Melanoma Elicits Tumor Immunity via Activation of Dendritic Cells by the Release of High Mobility Group Box 1," Oncotarget, vol. 7, No. 25, 2016, pp. 37893-37905; doi:10.18632/oncotarget.9247.
Jayanthan, A. et al, "Aurora Kinases as Druggable Targets in Pediatric Leukemia: Heterogeneity in Target Modulation Activities and Cytotoxicity by Diverse Novel Therapeutic Agents," PLOS One, vol. 9, issue 7, Jul. 2014; e102741. doi:10.1371/journal.pone.0102741.
Chou, T-C, "Drug Combination Studies and Their Synergy Quantification Using the Chou-Talalay Method," Cancer Research, vol. 70, No. 2, Jan. 15, 2010, pp. 440-446; doi:10.1158/0008-5472.CAN-09-1947.
Lun, X. et al, "Double-Deleted Vaccinia Virus in Virotherapy for Refractory and Metastatic Pediatric Solid Tumors," Molecular Oncology, vol. 7, No. 5, 2013, pp. 944-954; doi:10.1016/j.molonc.2013.05.004.
Fennelly, C. et al, "Methods in Molecular Biology; Lysosomal Biology in Cancer," Author Manuscript, PMC, 2017; 1594:293-308; doi:10.1007/978-1-4939-6934-0_19.
Berge, S.M. et al, "Pharmaceutical Salts," Journal of Pharmaceutical Sciences, vol. 66, No. 1, Jan. 1977, pp. 1-19.
Yvart, J. et al, "I Rose Bengal: Its Use in the Evaluation of Infantile Jaundice," European Journal of Nuclear Medicine, vol. 6, 1981, pp. 355-359.
Wachter, E. et al, "Functional Imaging of Photosensitizers Using Multiphoton Microscopy," Proceedings of SPIE, Multiphoton Microscopy in the Biomedical Sciences II, vol. 4620, 2002, pp. 143-147.
Koevary, S.B., "Selective Toxicity of Rose Bengal to Ovarian Cancer Cells in Vitro," International Journal of Physiology, Pathophysiology and Pharmacology, vol. 4, No. 2, 2012, pp. 99-107.
Thompson, J.F. et al,"Chemoablation of Metastatic Melanoma Using Intralesional Rose Bengal," Melanoma Research, vol. 18, 2008, pp. 405-411.
Lippey, J. et al, "Intralesional PV-10 for In-Transit Melanoma—a Single Center Experience," Journal of Surgical Oncology, vol. 114, 2016, pp. 380-384.
Ross, M.I., "Intralesional Therapy with PV-10 (Rose Bengal) for In-Transit Melanoma," Journal of Surgical Oncology, vol. 109, No. 4, 2014, pp. 314-319; doi:10.1002/jso.23554.
Moreno, L. et al, "Accelerating Drug Development for Neuroblastoma—New Drug Development Strategy: An Innovative Therapies for Children with Cancer, European Network for Cancer Research in Children and Adolescents and International Society of Paediatric Oncology Europe Neuroblastoma Project," Expert Opinion on Drug Discovery, vol. 12, No. 8, Aug. 2017; pp. 801-811; doi: 10.1080/17460441.2017.1340269. Epub Jun. 26, 2017.
Park, J.R. et al, "Children's Oncology Group's 2013 Blueprint for Research: Neuroblastoma," Pediatric Blood & Cancer, vol. 60, No. 6, 2013, pp. 985-993; doi:10.1002/pbc.24433.
"Provectus Biopharmaceuticals Expands Global Patent Portfolio for Cancer Combination Therapy," Globe Newswire, Apr. 18, 2018, pp. 1-2. www.globenewswire.com/news-release/2018/04/18/1480692/0/en/PROVECTUS.
International Search Report re application No. PCT/US/2019/032435, dated Aug. 29, 2019.
Written Opinion re application No. PCT/US/2019/032435, dated Aug. 29, 2019.
Swift, L. et al, "In vitro and Xenograft Ant-Tumor Activity, Target Modulation and Drug Synergy Studies of PV-10 Against Refractory Pediatric Solid Tumors," ASCO 2018 poster, Abstract No. 10557, 2018.
Swift, L. et al, "Potent in vitro and Xenograft Antitumor Activity of a Novel Agent, PV-10, Against Relapsed and Refractory Neuroblastoma," OncoTargents and Therapy, vol. 12, 2019, pp. 1293-1307.
Murphy, M. et al, "Childhood and Adult Cancers: Contrasts and Commonalities," Maturitas, vol. 76, pp. 95-98, 2013.
Narendran, Aru, Curriculum Vitae, Jun. 2020.

* cited by examiner

Representative bioluminescence images of the IMR5 tumor treated with control (PBS), and PV10

IN VITRO AND XENOGRAFT ANTI-TUMOR ACTIVITY OF A HALOGENATED-XANTHENE AGAINST REFRACTORY PEDIATRIC SOLID TUMORS

CROSS-REFERENCE TO RELATED APPLICATION

This application claims priority from application Ser. No. 62/672,373 that was filed on May 16, 2018, whose disclosures are incorporated herein by reference.

BACKGROUND ART

The types of cancers that develop in children are often different from the types that develop in adults. Childhood cancers are often the result of DNA changes in cells that take place very early in life, sometimes even before birth. Genetic mutations that initiate cancer development can thus arise during the development of a fetus in utero. Unlike many cancers in adults, childhood cancers are not strongly linked to lifestyle or environmental risk factors.

In addition, children face unique issues during their treatment for cancer, after the completion of treatment, and as survivors of cancer. For example, children may receive more intense treatments, while their cancer and its treatments can have different effects on a child's growing body compared to an adult body. Children can respond differently to drugs used to control symptoms in adults.

Adolescents and young adults are often diagnosed with different types of cancer from either younger children or older adults. The incidence of specific cancer types varies widely across the adolescent and young adult age continuum. Some evidence suggests that adolescents and young adults with acute lymphoblastic leukemia may have better outcomes if they are treated with pediatric treatment regimens than if they receive adult treatment regimens.

Currently, children with relapsed or metastatic solid tumors such as Ewing sarcoma, neuroblastoma, osteosarcoma and rhabdomyosarcoma have a low overall survival rate of less than 30% [1]. Of the pediatric solid tumors, neuroblastoma is the most common extra-cranial cancer in children and a leading cause of death in children aged 1-4 years [2].

Neuroblastoma originates from sympathetic nervous tissue and is a very heterogeneous and complex disease [3]. Recent improvements in treatment of neuroblastoma have increased 5-year survival rates for non-high risk disease to over 90% [4]. However, more than 40% of patients presenting with neuroblastoma are considered high-risk and despite intensive treatment regimens, 5-year survival rates for these patients are below 50% [2, 4]. Additionally, the prognosis for relapsed neuroblastoma is dismal, with a 5-year survival rate of less than 10% [4].

Given the poor survival rates of pediatric patients with relapsed or metastatic solid tumors such as, in particular those with high-risk and relapsed neuroblastoma, novel therapeutic approaches for the treatment of these malignancies are urgently needed.

One useful anti-cancer agent group for adult cancerous tumors are the halogenated xanthenes, or the pharmaceutically acceptable salts thereof. See, U.S. Pat. Nos. 6,331,286, 7,390,668, and 7,648,695. Of those halogenated xanthenes, Rose Bengal disodium, (4,5,6,7-tetrachloro-2',4',5',7'-tetraiodofluorescein disodium; RB) has been found to be particularly effective and easily utilized. Because of the often times very different behavior of adult tumors from pediatric tumors, it is not known whether RB and similar halogenated xanthenes would be similarly effective when used against pediatric cancerous tumors.

PV-10 is a sterile 10% solution of (RB), in 0.9% saline, that has been used clinically to measure liver function in infants [5]. Previous studies have shown that PV-10 accumulates in lysosomes [6] and induces cell death in a range of adult cancers [7-11].

In a phase II clinical trial for patients with refractory metastatic melanoma, intralesional (IL) injection of PV-10 induced tumor regression with an overall response rate of 51% [12]. PV-10 also demonstrated efficacy in combination with radiotherapy in a phase II clinical trial for patients with in-transit or metastatic melanoma, with an overall response rate of 86.6% [13]. In addition to inducing direct cancer cell death, PV-10 has also been shown to induce a tumor-specific immune response in both mouse studies [7, 8, 14] and clinical trials [10, 12, 14, 15, 16].

BRIEF SUMMARY OF THE INVENTION

The present invention contemplates a method of treating a pediatric cancerous solid tumor in a mammalian subject. One method contemplates intralesionally administering an amount of a halogenated xanthene or a pharmaceutically acceptable salt thereof that elicits ablation of tumor cells of the administered tumor. A second method comprises the steps of intralesionally administering an amount of a halogenated xanthene or a pharmaceutically acceptable salt thereof that elicits ablation of tumor cells of the administered tumor. A tumor-inhibiting effective amount of a systemic anti-cancer medication that provides synergistic cytotoxicity with the halogenated xanthene is also administered systemically to the mammalian subject.

The two medications can be administered concurrently, or one can be administered before the other by about one to about four weeks. It is preferred to carry out the intralesional administration prior to the systemic administration by about one to about four weeks.

BRIEF DESCRIPTION OF THE DRAWINGS

In the drawings forming a portion of this disclosure

FIG. 1, including

FIG. 2, including In FIG. 2(A), neuroblastoma cell lines SK-N-AS, SK-N-BE(2) and IMR5, and the closely related neuroepithelioma cell line SK-N-MC were treated with either PBS (vehicle control), 50 µM or 100 µM PV-10 for 96 hours and observed by phase-contrast light microscopy. Studies were performed three times and representative images are shown. Scale bar equals 100 µm. In FIG. 2(B), neuroblastoma cell lines SK-N-AS, SK-N-BE(2) and IMR5, and the neuroepithelioma cell line SK-N-MC were treated with either PBS (vehicle control) or 100 µM PV-10 and observed by time-lapse video microscopy. Images were captured every 30 minutes for 48 hours. Cell number was counted and normalized to cell number at 0 hours. At least 350 cells were counted per treatment per study. Mean percentages of cell numbers calculated from three separate studies and standard errors of the means are shown.

Figure 3:
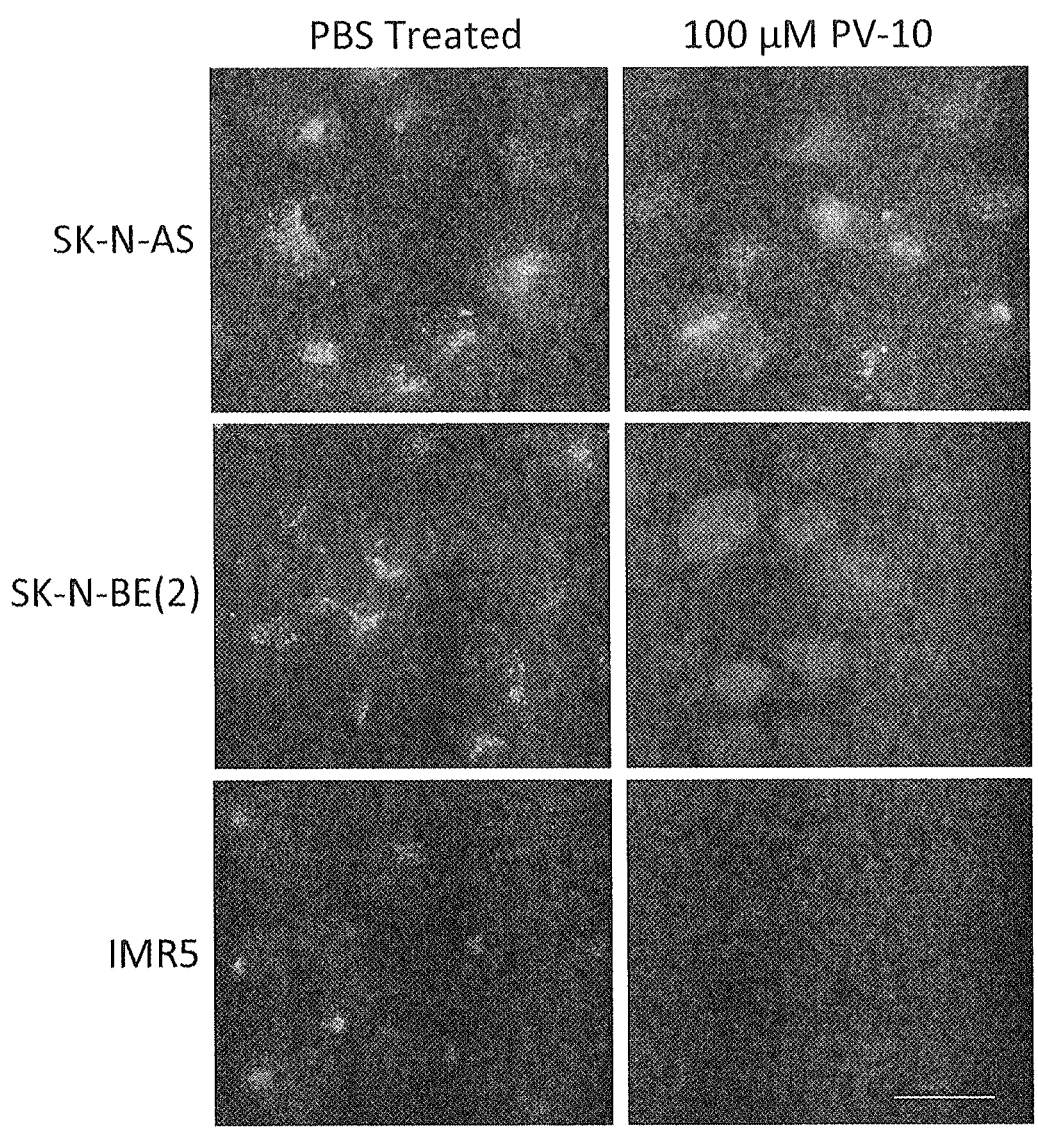

FIG. 3 illustrates that PV-10 disrupts lysosomes in cancerous cells. Neuroblastoma cell lines SK-N-AS, SK-N-BE(2) and IMR5 were treated with either PBS (vehicle control) or 100 µM PV-10 16 hours. Live cells were stained with nucleic acid stain Hoechst 33342 and LysoTracker® Green DND-26, which concentrates and fluoresces in acidic organelles, and observed by fluorescence microscopy. Scale bar equals 20 µm. Data presented are representative of three separate studies.

Figure 4A:
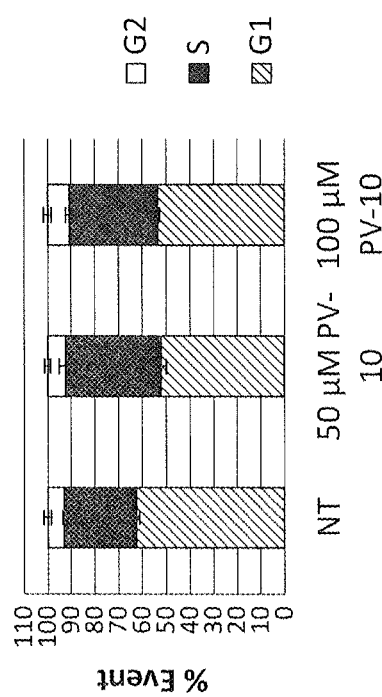
Figure 4B:
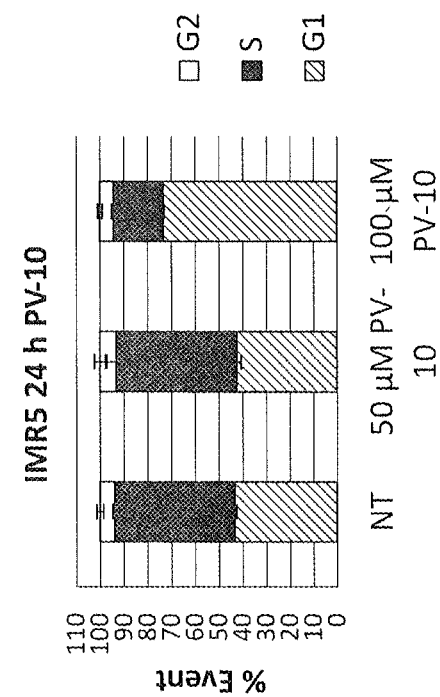
Figure 4C:
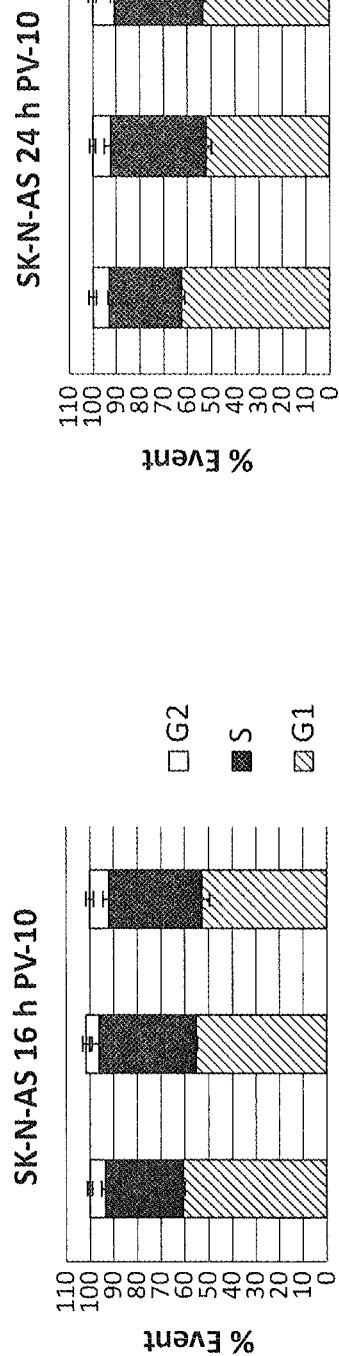
Figure 4D:
Figure 4E:
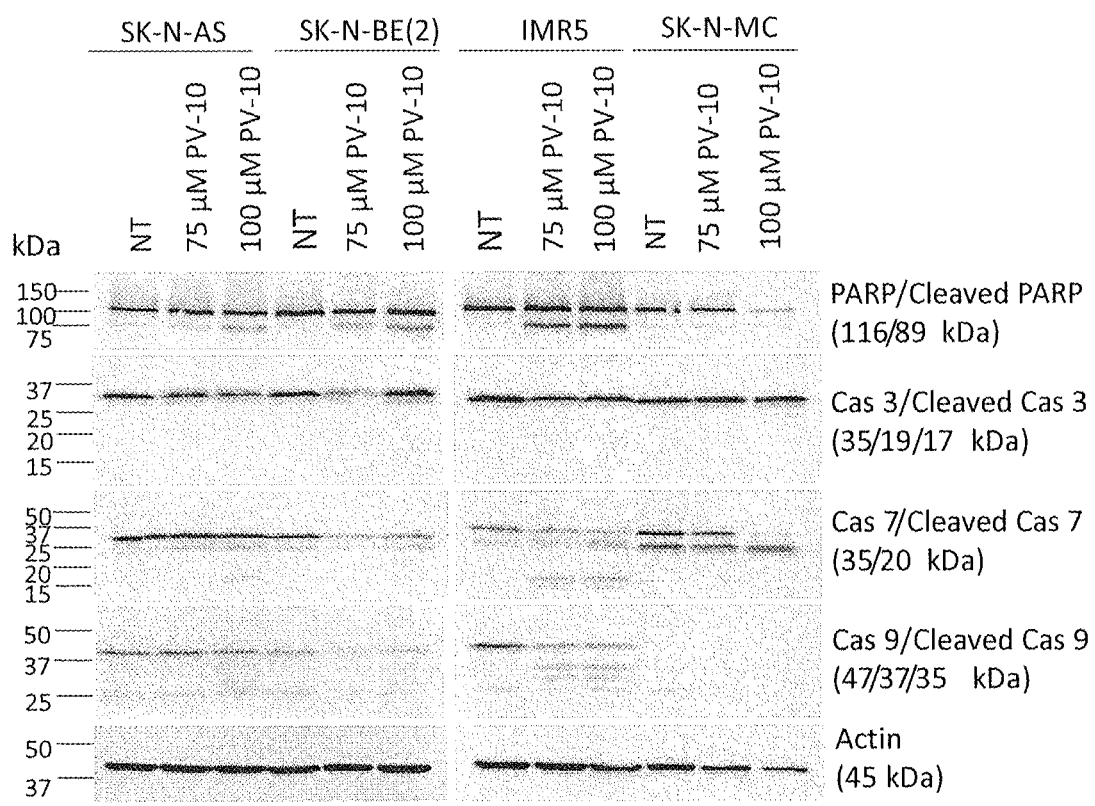
Figure 5A:
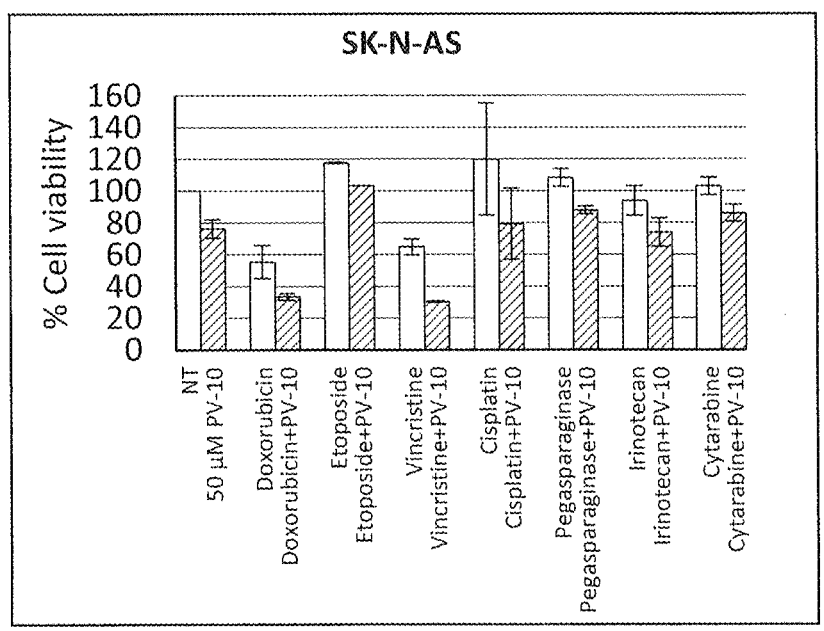
Figure 5B:
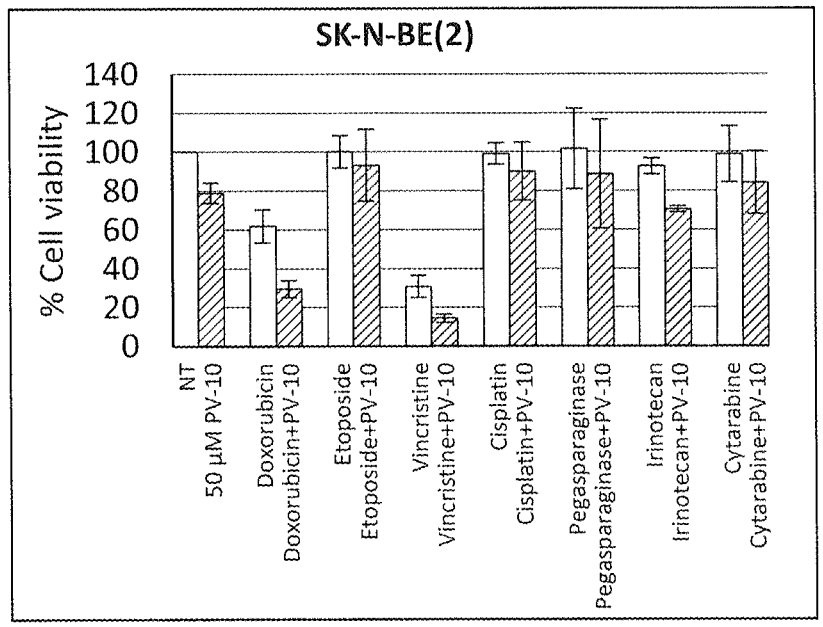
Figure 5C:
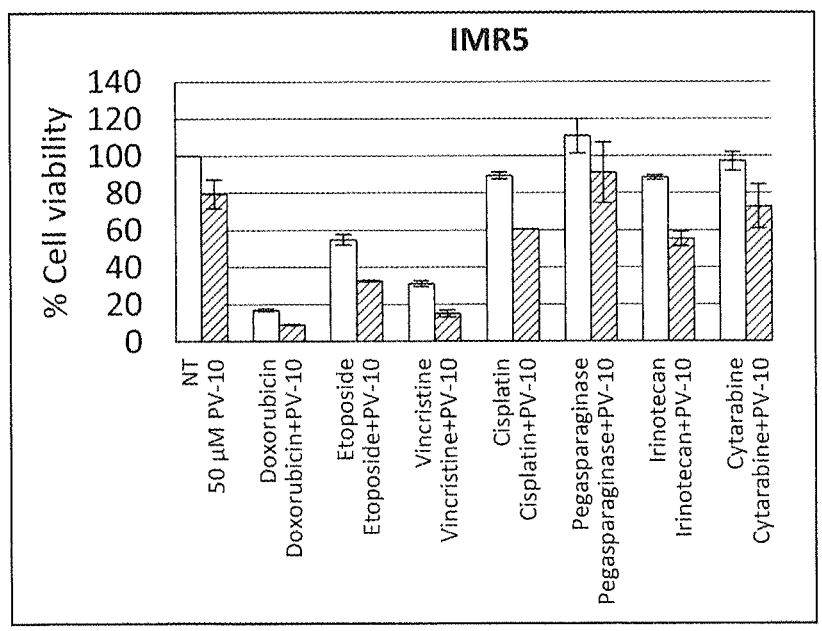
Figure 5D:
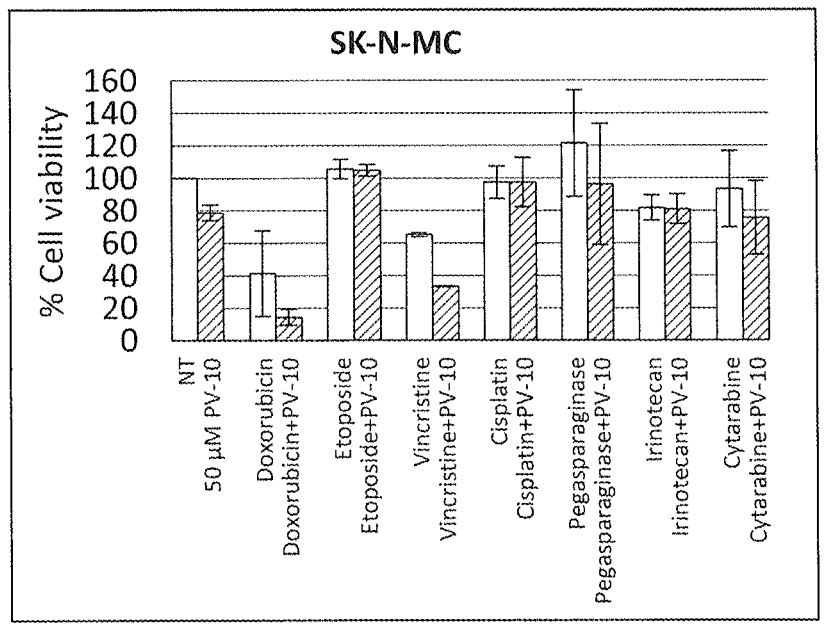
Figure 5E:
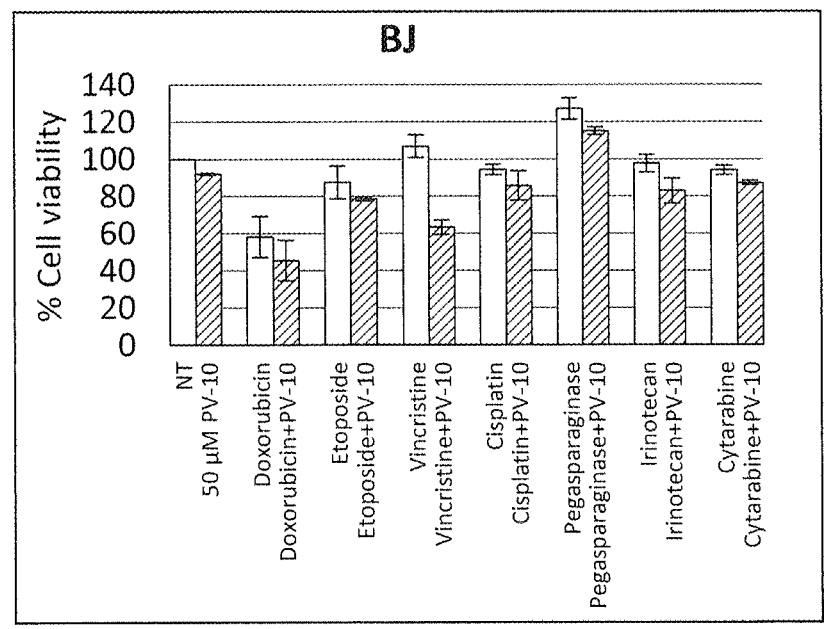

FIG. 4, including FIGS. 4A-4E, shows that PV-10 increases the percentage of cells in G1 phase of the cell cycle and induces cell death by apoptosis. In FIGS. 4A-4D, neuroblastoma cell lines SK-N-AS and IMR5 were treated with either PBS (vehicle control), 50 µM or 100 µM PV-10 for either 16 or 24 hours, stained with DAPI and analyzed by flow cytometry to detect cell cycle phase. Mean percentages of cells in either G1, S or G2/M phases of the cell cycle were calculated from three separate studies and standard errors of the means are shown. In FIG. 4E, neuroblastoma cell lines SK-N-AS, SK-N-BE(2) and IMR5, and the neuroepithelioma cell line SK-N-MC were treated with either PBS (vehicle control), 75 µM or 100 µM PV-10 for 24 hours. Total cell lysates were prepared and analyzed by western blotting to detect levels of total and cleaved poly-ADP ribose polymerase (PARP), caspase 3, caspase 7 and caspase 9. Actin was used as a loading control. Molecular masses are indicated in kilodaltons (kDa). Data presented are representative of two separate studies.

FIGS. 5A-5E illustrate that PV-10 treatment is synergistic with different anti-cancer agent treatments. Neuroblastoma cell lines SK-N-AS, SK-N-BE(2) and IMR5, neuroepithelioma cell line SK-N-MC and the normal fibroblast cell line BJ (FIGS. 5A-5E, respectively) were treated with 0.1 µM of seven different anti-cancer agents either alone or in combination with 50 µM PV-10. Cells were treated for 96 hours and cell viability was measured by alamar blue®. Percent cell viability was normalized to treatment with PBS (vehicle control). Mean percentages of cell viability calculated from two separate studies and standard errors of the means are shown.

Figure 6A:
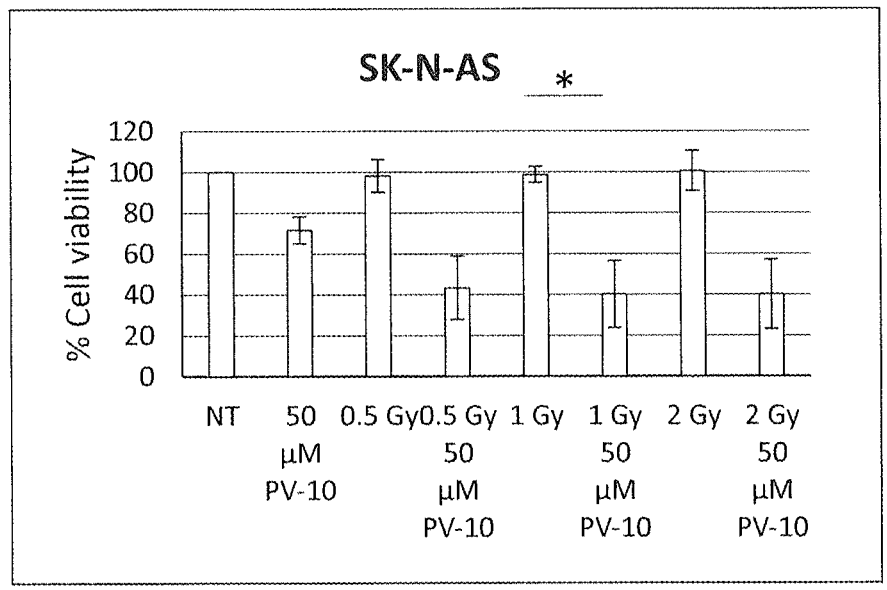
Figure 6B:
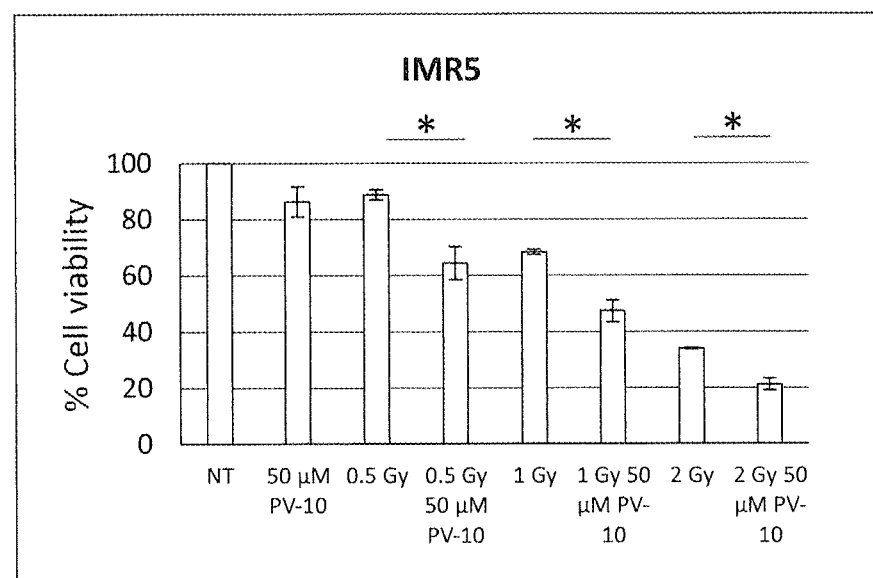

FIG. 6, including FIGS. 6A and 6B, shows that PV-10 treatment enhances the effect of irradiation. Neuroblastoma cell lines SK-N-AS (FIG. 6A) and IMR5 (FIG. 6B) were pre-treated with either PBS (vehicle control) or 50 µM PV-10 for 4 hours. Cells were then irradiated with either 0.5, 1 or 2 Gy and cultured for a further 92 hours. Cell viability was measured by alamar blue®. Mean percentages of cell viability calculated from three separate studies and standard errors of the means are shown. Asterisks show significant differences, paired student's t-test, p<0.05.

Figure 7A:
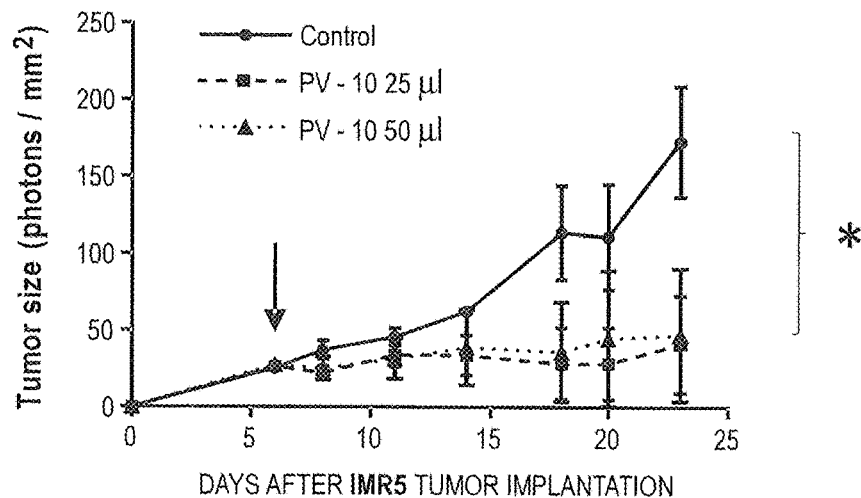
Figure 7B:
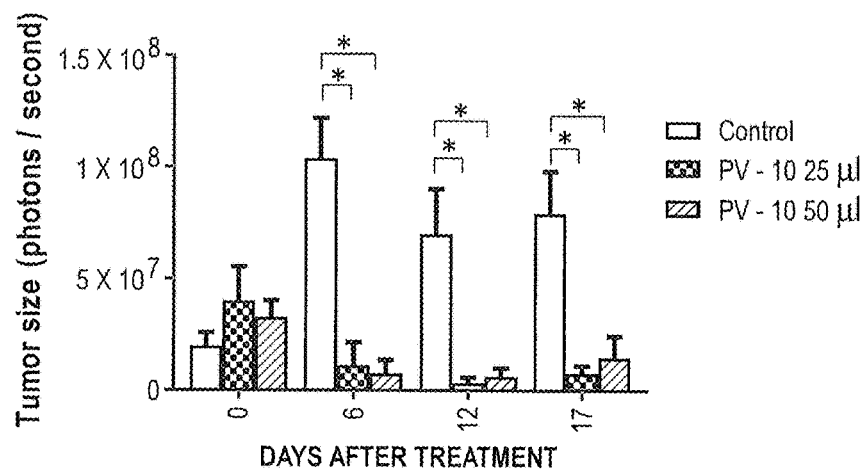
Figure 7C:
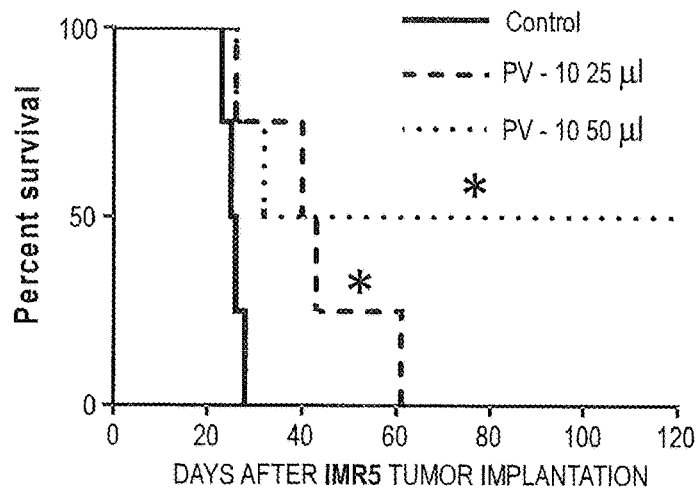
Figure 7D:
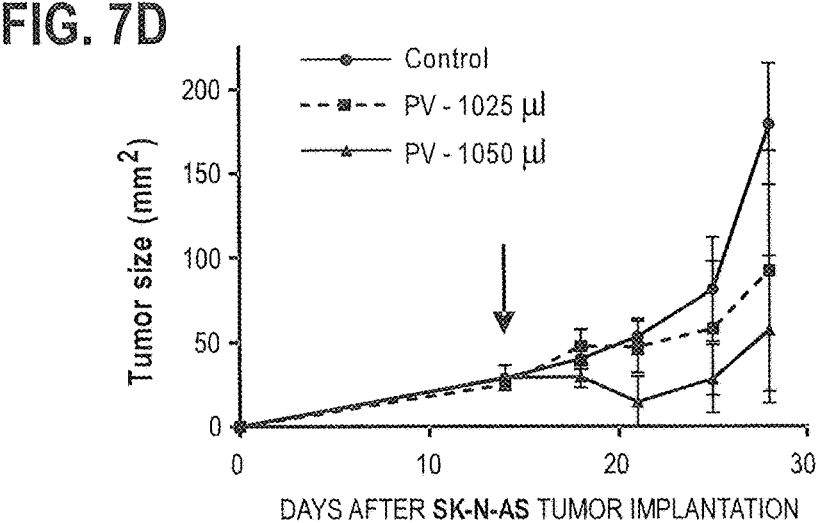
Figure 7E:
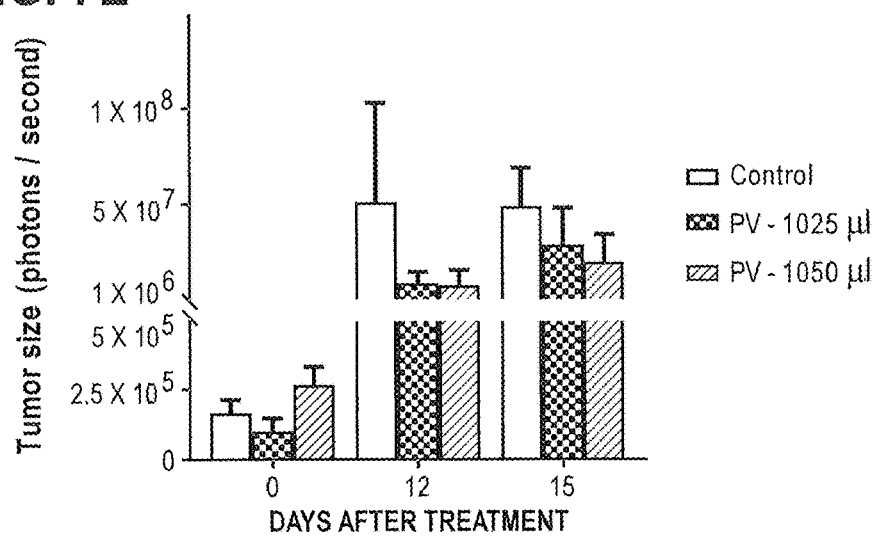
Figure 7F:
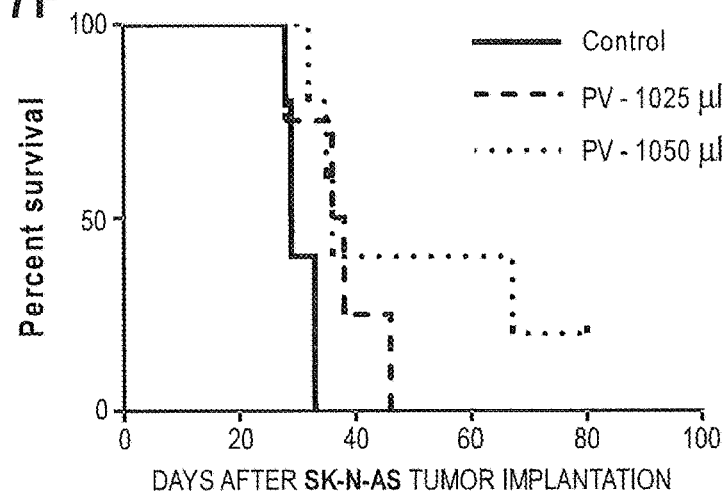

FIG. 7, including FIGS. 7A-7F, illustrates that PV-10 treatment induces tumor regression in vivo. CB17 SCID mice (n=4 per group) were subcutaneously injected on the right flank with either IMR5-mCherryFluc or SK-N-AS-mCherryFluc cells. When tumor size was at least 5×5 mm, tumors were injected with either 50 µl PBS (vehicle control), 25 µl PV-10 or 50 µl PV-10. In FIG. 7A, IMR5-mCherryFluc tumor growth was measured using a Vernier caliper. Arrow indicates treatment day (day 6). Mean tumor size and standard error of the mean are shown. Asterisks show significant differences, unpaired student's t-test, p<0.05. In FIG. 7B, IMR5-mCherryFluc tumor growth was measured using the Xenogen IVIS® 200 system to detect bioluminescent signal following intraperitoneal injection with D-luciferin. Mean tumor size and standard error of the mean are shown. FIG. 7C shows a survival curve for mice with IMR5-mCherryFluc tumors. Asterisks show significant differences, Log-rank (Mantel-Cox) test, p<0.05. In FIG. 7D, SK-N-AS-mCherryFluc tumor growth was measured over time in days using a Vernier caliper. Arrow indicates treatment day (day 14). Mean tumor size and standard error of the mean are shown. In FIG. 7E, SK-N-AS-mCherryFluc tumor growth at zero, 12 and 15 days post treatment was measured using the Xenogen IVIS® 200 system to detect bioluminescent signal following intraperitoneal injection with D-luciferin. Mean tumor size and standard error of the mean are shown. FIG. 7F shows a survival curve for mice with SK-N-AS-mCherryFluc tumors.

Figure 8:
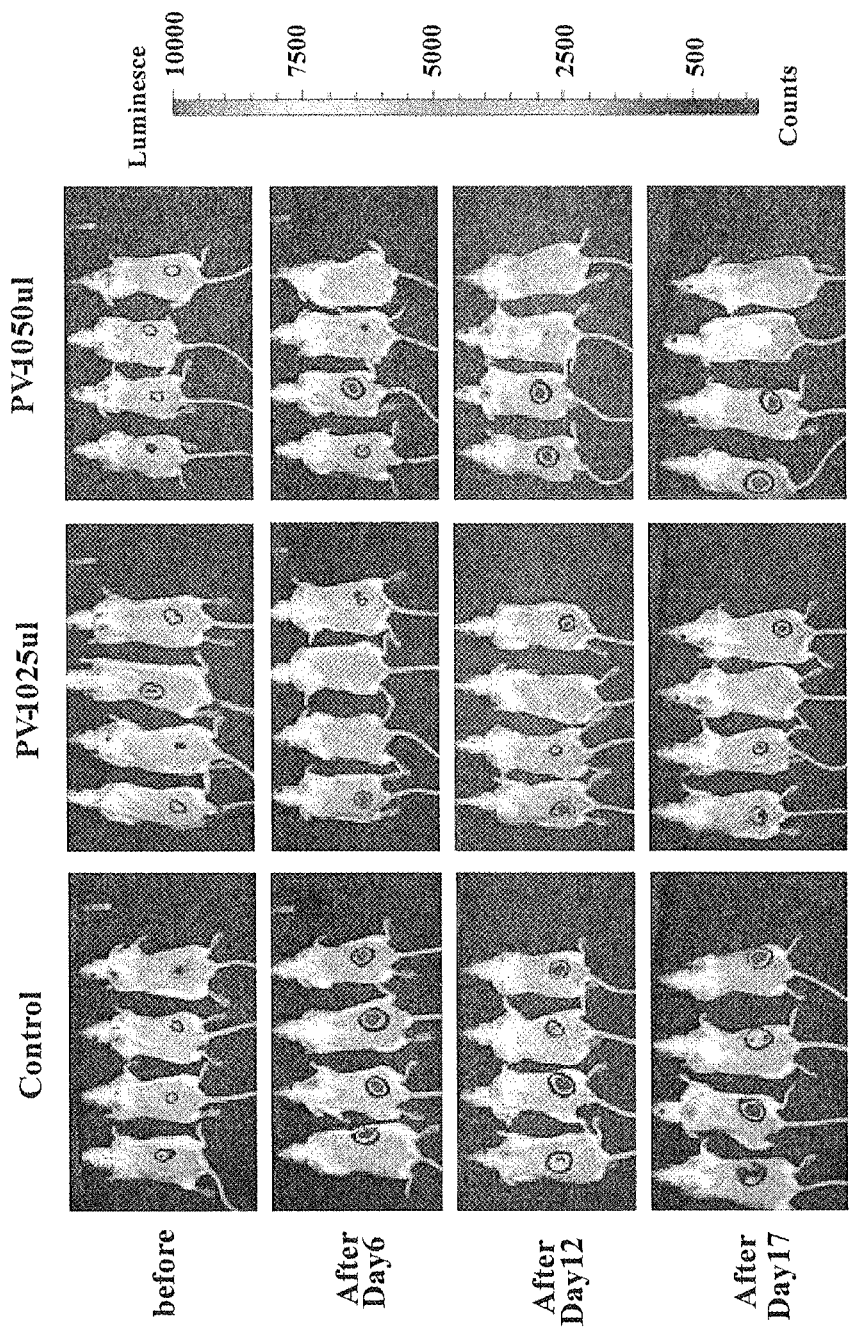

FIG. 8 shows a group of mouse photographs in each experimental group described by FIG. 7 where the bioluminescent image depicts active flank tumors in each of the experimental groups (PBS Control, PV-10 25 µL and PV-10 50 µL dose) after day 6, day 12 and day 17.

DETAILED DESCRIPTION OF PREFERRED EMBODIMENTS

The present invention contemplates a method of treatment of a pediatric solid tumor with a pharmaceutical composition that contains a tumor-inhibiting effective amount of a halogenated xanthene or pharmaceutically acceptable salt thereof such as Rose Bengal (RB, 4,5,6,7-tetrachloro-2',4',5',7'-tetraiodofluorescein disodium) into the tumor (intralesionally). The Rose Bengal-containing composition can be utilized as the sole treating agent, but in some preferred embodiments, RB is preferably coupled with another antitumor modality such as a systemic anti-cancer medication that can be a small molecule (non-proteinaceous, less than about 1000 grams/mole) or a proteinaceous molecule such as an antibody or an enzyme, ionizing radiation therapy or so-called checkpoint inhibition antibody therapy. As shown herein, several of these combinations have exhibited synergistic toxicities toward pediatric tumors.

Halogenated Xanthene

A contemplated halogenated xanthene such as of Rose Bengal (4,5,6,7-tetrachloro-2',4',5',7'-tetraiodofluorescein) that is particularly preferred, or another halogenated xanthene, including erythrosin B, phloxine B, 4,5,6,7-tetrabromo-2',4',5',7'-tetraiodofluorescein, 2',4,5,6,7-pentachloro-4',5',7'-triiodofluorescein, 4,4',5,6,7-pentachloro-2',5',7'-triiodofluorescein, 2',4,5,6,7,7'-hexachloro-4',5'-diiodofluorescein, 4,4',5,5',6,7-hexachloro-2',7'-diiodofluorescein, 2',4,5,5',6,7-hexachloro-4',7'-diiodofluorescein, 4,5,6,7-tetrachloro-2',4',5'-triiodofluorescein, 4,5,6,7-tetrachloro-2',4',7'-triiodofluorescein, 4,5,6,7-tetrabromo-2',4',5'-triiodofluorescein, and 4,5,6,7-tetrabromo-2',4',7'-triiodofluorescein is present dissolved or dispersed in an appropriate pharmaceutical composition.

A preferred form, Rose Bengal disodium, has the following structural formula:

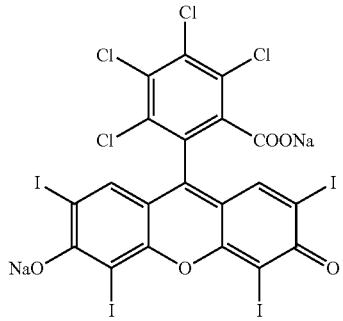

Certain details of this preferred embodiment for a contemplated composition are described in U.S. Pat. Nos. 5,998,597, 6,331,286, 6,493,570, and 8,974,363, whose disclosures are incorporated by reference herein in their entireties.

Delivery of the halogenated xanthene component of a contemplated composition is most favorable when the composition has a pH value close to physiologic pH (i.e., approximately pH 7), and especially when the pH value is greater than about 4, thereby assuring that a halogenated xanthene remains in dibasic form in the composition. Thus, in a preferred embodiment, the pH value of the composition is about 4 to about 10, and more preferably about 5 to about 9, and most preferably about pH 6 to about pH 8.

A hydrophilic vehicle is preferred for the medicament to maximize preference for partitioning of the halogenated xanthene component into tissue. Accordingly, in a preferred embodiment, the vehicle contains a minimum of non-hydrophilic components that might interfere with such partitioning.

Accordingly, a preferred formulation of the composition contains, in a hydrophilic, preferably water-containing, vehicle a halogenated xanthene such as of Rose bengal (4,5,6,7-tetrachloro-2',4',5',7'-tetraiodofluorescein) that is particularly preferred, or another halogenated xanthene, including erythrosin B, phloxine B, 4,5,6,7-tetrabromo-2',4',5',7'-tetraiodofluorescein, 2',4,5,6,7-pentachloro-4',5',7'-triiodofluorescein, 4,4',5,6,7-pentachloro-2',5',7'-triiodofluorescein, 2',4,5,6,7,7'-hexachloro-4',5'-diiodofluorescein, 4,4',5,5',6,7-hexachloro-2',7'-diiodofluorescein, 2',4,5,5',6,7-hexachloro-4',7'-diiodofluorescein, 4,5,6,7-tetrachloro-2',4',5'-triiodofluorescein, 4,5,6,7-tetrachloro-2',4',7'-triiodofluorescein, 4,5,6,7-tetrabromo-2',4',5'-triiodofluorescein, and 4,5,6,7-tetrabromo-2',4',7'-triiodofluorescein in an appropriate pharmaceutical composition.

A preferred form, Rose Bengal disodium, has the following formula:

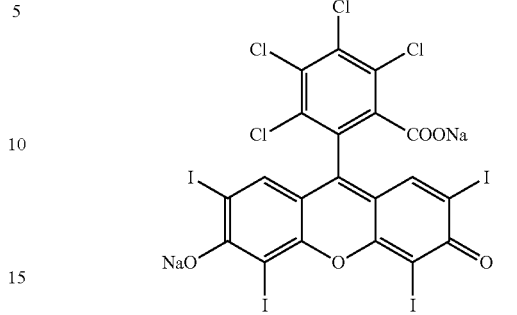

Certain details of this preferred embodiment for the pharmaceutical composition are described in U.S. Pat. Nos. 5,998,597, 6,331,286, 6,493,570, and 8,974,363, whose disclosures are incorporated by reference herein in their entireties.

A contemplated halogenated xanthene-containing composition typically contains the halogenated xanthene at a concentration of about 0.1% (w/v) to about 20% (w/v) in an aqueous medium. The pharmaceutical halogenated xanthene-containing composition preferably includes a water-soluble electrolyte comprising at least one cation selected from the group consisting of sodium, potassium, calcium and magnesium and at least one anion selected from the group consisting of chloride, phosphate and nitrate, wherein the electrolyte is at a concentration of between about 0.1% (w/v) and about 2% (w/v).

A third ingredient is a water-soluble electrolyte selected from sodium, potassium, calcium and magnesium chlorides, phosphates, and nitrates, wherein the electrolyte is present at a concentration of about 0.1 to about 2% by weight, or alternately at a level sufficient to provide an osmolality of greater than approximately 100 mOsm/kg up to about 600 mOsm/kg. More preferably, the osmolality of the medicament composition is greater than 250 mOsm/kg, and most preferably approximately 300-500 mOsm/kg. The electrolyte is preferably sodium chloride. The electrolyte is preferably present at a concentration of about 0.5 to about 1.5%, and even more preferably at a concentration of about 0.8 to about 1.2%, and most preferably at a concentration of approximately 0.9% as is present in physiological saline.

The aqueous medium of the composition is preferably only water that meets the criteria for use in injection. Up to about 20 percent by volume of the vehicle can be one or more $C_1$-$C_6$ mono- or polyhydric alcohols such as methanol, ethanol, propanol, isopropanol, butanol, sec-butanol, glycerol, ethylene glycol, propylene glycol, 1,2-butanediol, 2,3-butanediol, erytritol, threitol, trimethylolpropane, sorbitol and the like. More preferably, an alcohol is present in a contemplated composition at less than about 10 percent by volume of the vehicle, and more preferably at less than about 5 percent by volume.

Looked at alternatively, the present invention utilizes a compound of Formula 1, below, in which $R_1$ is independently F, Cl, Br, I, H or $C_1$-$C_4$ alkyl; $R_2$, $R_3$, $R_4$, and $R_5$ are independently Cl, H or I with at least one substituent selected from $R_2$, $R_3$, $R_4$, $R_5$ being I and at least one is Cl or H; and $R_6$ is independently H or $C_1$-$C_4$ alkyl; $R^{11}$ is H or $C_1$-$C_4$ alkyl; $R^{12}$ is H or $C_1$-$C_7$ acyl; and all (a) tautomeric forms; (b) atropisomers, (c) closed lactone forms as depicted in Formula 2 (below), (d) enantiomers of lactone forms depicted in Formula 2, and (e) pharmaceutically acceptable salts thereof.

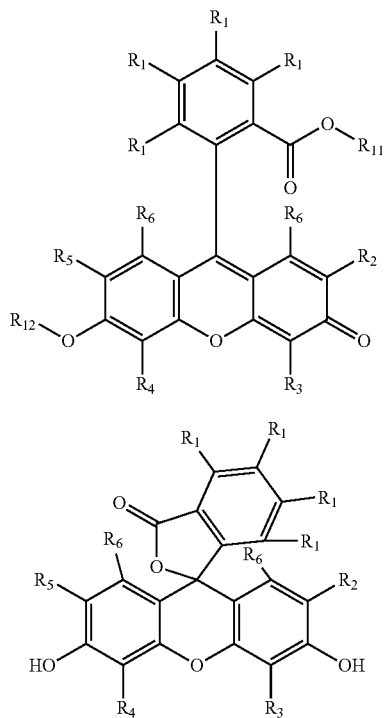

FORMULA 1

FORMULA 2

The term "physiologically acceptable salt" "pharmaceutically acceptable salt" in their various grammatical forms refer to any non-toxic cation such as an alkali metal, alkaline earth metal, and ammonium salt commonly used in the pharmaceutical industry, including the sodium, potassium, lithium, calcium, magnesium, barium, ammonium and protamine zinc salts, which can be prepared by methods known in the art. A contemplated cation provides a water-soluble xanthene salt. Preferably, the salts are sodium, potassium, calcium and ammonium in either the mono or dibasic salt form. The reader is directed to Berge, *J. Pharm. Sci.* 1977 68(1):1-19 for lists of commonly used physiologically (or pharmaceutically) acceptable acids and bases that form physiologically acceptable salts with pharmaceutical compounds.

The pH value of the halogenated xanthene pharmaceutical composition can be regulated or adjusted by any suitable means known to those of skill in the art. The composition can be buffered or the pH value adjusted by addition of acid or base or the like. As the halogenated xanthenes, or physiologically acceptable salts thereof, are weak acids, depending upon halogenated xanthene concentration and/or electrolyte concentration, the pH value of the composition may not require the use of a buffer and/or pH value-modifying agent. It is especially preferred, however, that the composition be free of buffer, allowing it to conform to the biological environment once administered.

It is also preferred that the pharmaceutical composition not include any preservatives, many of which can deleteriously interfere with the pharmaceutical composition or formulation thereof, or may complex or otherwise interact with or interfere with the delivery of the halogenated xanthene composition active component. To the extent that a preservative is used, imidurea is a preferred preservative as it does not interact with halogenated xanthenes, either in the pharmaceutical composition or upon administration.

A contemplated treatment method is utilized on a mammal in need thereof. A treated mammal can be a primate such as a human, an ape such as a chimpanzee or gorilla, a monkey such as a cynomolgus monkey or a macaque, a laboratory animal such as a rat, mouse or rabbit, a companion animal such as a dog, cat, horse, or a food animal such as a cow or steer, sheep, lamb, pig, goat, llama or the like.

Each contemplated composition is typically administered repeatedly in vivo to a mammal in need thereof until the treated solid cancerous tumor is diminished to a desired extent, such as cannot be detected. Thus, the administration to a mammal in need can occur a plurality of times within one day, daily, weekly, monthly or over a period of several months to several years as directed by the treating physician.

A contemplated halogenated xanthene compound when injected directly into a tumor is typically taken up by and accumulates in the cancer cells' lysosomes and induces cell death by apoptosis or another mechanism. In causing cancer cell death, the cells disintegrate or ablate. It is believed that that ablation of cell fragments specifically stimulates the mammal's immune system to the antigens displayed on the ablated cell fragments such that tumors distant from the site of intratumoral (intralesional) injection are recognized and are also killed.

As has also been noted previously, a preferred contemplated composition of a halogenated xanthene or a pharmaceutically acceptable salt thereof is referred to as PV-10™. PV-10™ is a sterile 10% solution of Rose Bengal (RB, 4,5,6,7-tetrachloro-2',4',5',7'-tetraiodofluorescein disodium) in 0.9% saline.

A tumor-inhibiting effective amount of a systemic anti-cancer medication that provides synergistic cytotoxicity when used in combination with the halogenated xanthene is administered to the mammalian subject in need and can be formulated using usual liquid, gel, solid or other formats. Thus, it is to be understood that a systemic anti-cancer medication can illustratively be administered orally as by tablet or liquid composition, by injection i.v., i.m., s.c., intraperitoneally, via ionizing radiation, or by any other form that provides an effective amount of the anti-cancer medication to the subject.

Systemic Anti-Cancer Medication

Systemic anti-cancer medication that is a small molecule (non-proteinaceous, less than about 1000 grams/mole) or a larger proteinaceous molecule, is administered to the subject mammal to be treated such that the medication spreads throughout the subject's body as compared to the localized administration that occurs with an intralesional administration of a halogenated xanthene. Illustrative small molecule anti-cancer medications include doxorubicin, etoposide, vincristine, cisplatin, irinotecan and cytarabine that were used herein, whereas an exemplary proteinaceous molecule is asparaginase. Of those medications, doxorubicin, etoposide and vincristine appeared to synergize with treatment with a sub-lethal dose of PV-10, and are preferred.

A useful effective dosage of a small molecule, systemic anti-cancer medication is the dosage set out in the labeling information of a FDA-, national- or international agency-approved medication. Typically, monotherapy dose schedules are set by determining the maximum tolerated dose (MTD) in early-stage clinical trials. The MTD (or a close variation thereon) is then promulgated to later-stage clinical trials for assessment efficacy and more detailed assessment of safety. These MTDs frequently become the established therapeutic dose upon completion of clinical testing. However, because the small molecule, systemic anti-cancer medication is contemplated for use with PV-10, a MTD is the maximal amount that would be used, and that amount is to be titrated downward following usual procedures.

Exemplary dosing schedules for a number of systemic anti-cancer medications that can be combined in the present invention with localized PV-10 therapy are provided in Table A, below. It is noted that several of the medications listed below are "small molecules" as defined above, whereas others are large, proteinaceous molecules such as antibodies. They are nonetheless administered systemically.

The proteinaceous anti-cancer medications noted below typically inhibit an inflammatory response caused by chemokines such as the TNF family and the interleukin family.

TABLE A

Exemplary systemic immunomodulatory or targeted anticancer agents

| Systemic Agent | Typical Dose Schedule |
| --- | --- |
| adalimumab | 80 mg initial dose followed in 1 week by 40 mg every other week SQ |
| brodalumab | 210 mg subcutaneously (SC) at Weeks 0, 1, and 2, then 210 mg SC q2wk |
| certolizumab pegol | 400 mg initially and at weeks 2 and 4 followed by 200 mg every other week or 400 mg Q4 weeks maintenance SQ |
| etanercept | 50 mg twice weekly for 3 months followed by 50 mg once weekly SQ |
| golimumab | 50 mg once a month SQ |
| guselkumab | 100 mg subcutaneous injection once every 8 weeks, after starter doses at weeks 0 and 4 |
| infliximab | 5 mg/kg given as an IV induction regimen at 0, 2, and 6 weeks followed by a maintenance regimen of 5 mg/kg every 8 weeks thereafter |
| ixekizumab | 160 mg initial dose followed Q2 weeks with 80 mg until week 12 then 80 mg Q4 weeks SQ |
| sarilumab | 200 mg every 2 weeks as a subcutaneous injection |
| secukinumab | 300 mg every week for 4 weeks then 300 mg every 4 weeks SQ |
| ustekinumab | Less than 100 kg: 45 mg initially, week 4 followed by 45 mg every 12 weeks SQ<br>More than 100 kg: 90 mg initially, week 4 followed by 90 mg every 12 weeks SQ |
| apremilast | Titrated dose over 5 days to work up to 30 mg twice daily PO |
| methotrexate | Weekly single oral, IM or IV 10 to 25 mg per week or divided 2.5 mg dose at 12 hour intervals for three doses |
| cyclosporine | Initial dose 2.5 mg/kg/day taken twice daily as divided (BID); dose titrated up to 4 mg/kg/day BID if response and laboratory abnormalities don't ensue. |
| azathioprine | Used off label for skin diseases, 1.0 mg/kg oral or IV as a single dose or twice a day, dose maximum is 2.5 mg/kg/day. |

Because of additive or synergistic effects, the combination therapies and method of treatment of the present invention generally permit use of the systemic agent at a level at or below the typical dose schedule for the systemic agent, such as those described in Table A, when used with a local topical therapy, such as that described below. However, the dosing schedules provided in Table A provide a useful guide for beginning treatment from which dosages can be titrated to lessened amounts as seen appropriate by the physician caring for a given patient.

Ionizing Radiation Treatment

The results reported herein show that combining treatment of PV-10 with ionizing radiation also enhanced the cytotoxicity of the treatment as a whole. For the in vitro studies here, the neuroblastoma cells were first contacted with a sub-lethal dose of PV-10 for a time period of four hours and then irradiated with dosages of 0.5, 1 or 2 Gray of ionizing radiation.

It is to be understood that this treatment regimen was illustrative and has proven the concept of this combination of treatments. Workers of ordinary are able to utilize these effects and scale the treatment accordingly.

Checkpoint Antibody Inhibitors

A still further combination treatment regimen utilizes the administration of PV-10 and a checkpoint antibody inhibitor, that can be viewed as a special systemic anti-cancer medication. A useful checkpoint antibody inhibitor is a humanized monoclonal antibody whose administration permits the immune system to recognize the cancer cells as foreign and assist in eliminating those cancer cells from the body.

Some checkpoint inhibitor antibodies target the PD-1 (programmed cell death protein 1) receptor on the surface of T cells or the ligand for that receptor PD-L1. Exemplary of these monoclonals are pembrolizumab and nivolumab that inhibit PD-1. Two antibodies that target PD-L1 are atezolizumab, avelumab and durvalumab. Another group of checkpoint inhibitor monoclonal antibodies includes ipilimumab tremelimumab that target CTLA-4, a protein receptor that downregulates the immune system.

These anti-cancer medications are also usually used systemically. The MTD as described in the package labels for these medications can again be a starting dosage that is typically titrated downward during trials as discussed previously.

Dosing

A PV-10 companion systemic medication can be administered as often as is needed or tolerated by the recipient subject. Small molecule medications typically have relatively short in vivo half-lives or minutes to days. On the other hand, the checkpoint inhibitor antibodies often have in vivo half-lives of one to three weeks.

The in vivo biological lifetime of Rose Bengal is understood to be a few minutes in the rat. However, because intralesional PV-10 administration is known to induce a T cell immune enhancement, the effect of an administration of PV-10 can last for months or more, via memory T cells.

As a consequence of the various half-lives of the compositional regents, it is preferred to treat first with PV-10 and then one or more combination medicaments. The combination medicament is preferably administered about 1 to about 4 weeks after the administration of the PV-10 so that the induced immune activation can at least begin.

Pretreatment with a systemic anti-cancer medication can also be useful. Here the systemic anti-cancer agent can initiate the immune response that is enhanced by later treatment with PV-10. Here, it is also preferred that a time between the first two treatment be about 1 to about 4 weeks.

The two medications can also be administered at about the same time, concurrently, which can be simultaneously to within about one week of each other.

Results

PV-10 Inhibits Growth of Pediatric Solid Tumor Cell Lines

Ewing sarcoma, neuroblastoma, osteosarcoma, rhabdomyosarcoma and normal fibroblast cell lines and a normal primary bone marrow sample were treated with different concentrations of PV-10 (3.125-400 µM) for 96 hours and cell viability was measured using alamar blue® (FIGS. 1A-1E) to determine the effects of PV-10 on pediatric solid tumors. PV-10 decreased cell viability in a concentration-dependent manner in all cell lines tested. $IC_{50}$ values were calculated for all solid tumor cell lines examined. Table 1, below, shows values for PV-10 treated pediatric solid tumor cell lines 96 hours post-treatment. As is seen, the values ranged from 45-108 µM, with a mean of 70 µM.

TABLE 1

| Cell Line | Cell Type | PV-10 $IC_{50}$ µM |
|---|---|---|
| SK-PN-DW | Ewing sarcoma | 80 |
| SK-ES | Ewing sarcoma | 45 |
| SK-N-AS | Neuroblastoma | 85 |
| LAN1 | Neuroblastoma | 80 |
| SK-N-BE(2) | Neuroblastoma | 73 |
| IMR5 | Neuroblastoma | 73 |
| SHEP | Neuroblastoma | 73 |
| SK-N-SH | Neuroblastoma | 65 |
| SK-N-MC | Neuroepithelioma | 45 |
| 143B | Osteosarcoma | 108 |
| HOS | Osteosarcoma | 75 |
| RD | Rhabdomyosarcoma | 56 |
| RH30 | Rhabdomyosarcoma | 51 |

By contrast, $IC_{50}$ values for the normal fibroblast cell lines and primary bone marrow samples were higher and ranged from 73-143 µM, with a mean of 104 µM (Table 2), below. Table 2 provides one-half maximal inhibitory concentration ($IC_{50}$) values for PV-10 treated normal fibroblast cell lines and a primary bone marrow sample 96 hours post-treatment.

TABLE 2

| Cell Line | Cell Type | PV-10 $IC_{50}$ (µM) |
|---|---|---|
| BJ | Normal fibroblast (foreskin) | 143 |
| Primary bone marrow | Normal primary fibroblasts | 136 |
| WI38 | Normal fibroblast (lung) | 93 |
| WI38 hTERT | Normal fibroblast (lung) hTERT transformed | 75 |
| BJ hTERT | Normal fibroblast (foreskin) hTERT transformed | 73 |

PV-10 is Cytotoxic to Neuroblastoma Cell Lines

Having identified that PV-10 is cytotoxic to pediatric solid tumor cell lines, neuroblastoma was focused upon because it is the most common extra-cranial cancer in children. Whether PV-10 was cytotoxic or cytostatic to neuroblastoma cell lines was investigated. Four different cell lines were chosen for study, three neuroblastoma cell lines [SK-N-AS, SK-N-BE(2) and IMP5] that have different mutations and different sensitivities to PV-10 based on $IC_{50}$ values, and one neuroepithelioma cell line (SK-N-MC) that was very sensitive to PV-10 based on its $IC_{50}$ value.

Figure 1A:
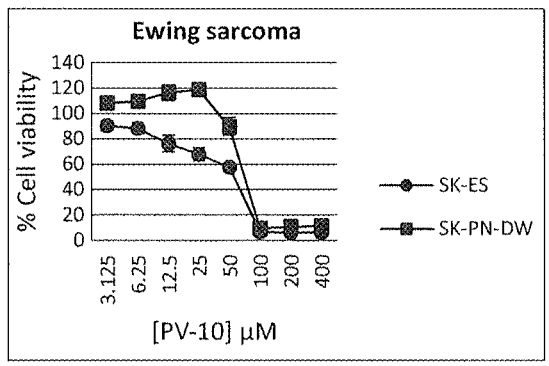
FIGS. 1A-1E, illustrates that PV-10 decreases cell viability in pediatric solid tumor cell lines. Different pediatric solid tumor cell lines (Ewing sarcoma, neuroblastoma, osteosarcoma and rhabdomyosarcoma), normal fibroblast cell lines and a primary bone marrow sample were treated with increasing concentrations (3.125-400 µM) of PV-10 for 96 hours. Cell viability was measured by alamar blue® assay. Percent cell viability was normalized to corresponding treatment with PBS (vehicle control). Mean percentages of cell viability were calculated from three separate studies and standard errors of the means are shown.
Figure 1B:
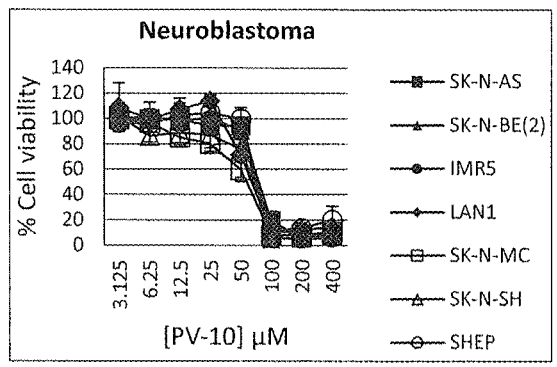
Figure 1C:
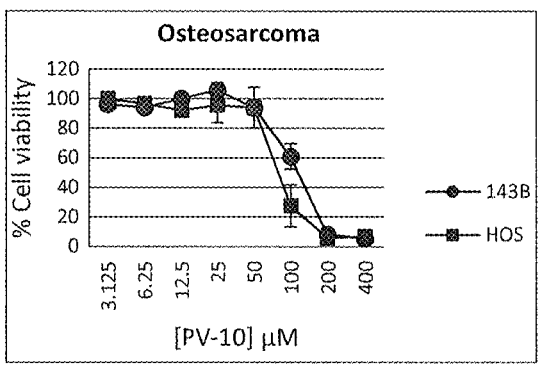
Figure 1D:
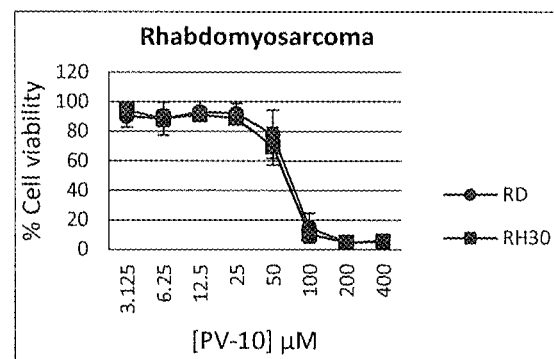
Figure 1E:
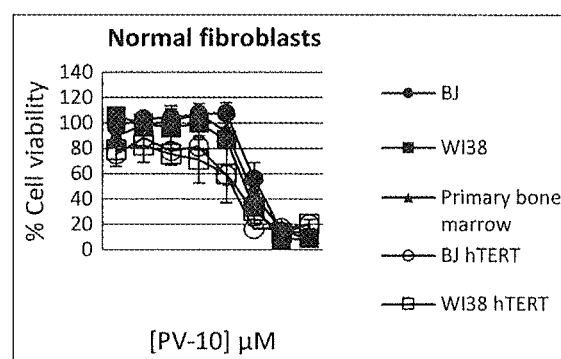
Figure 2A:
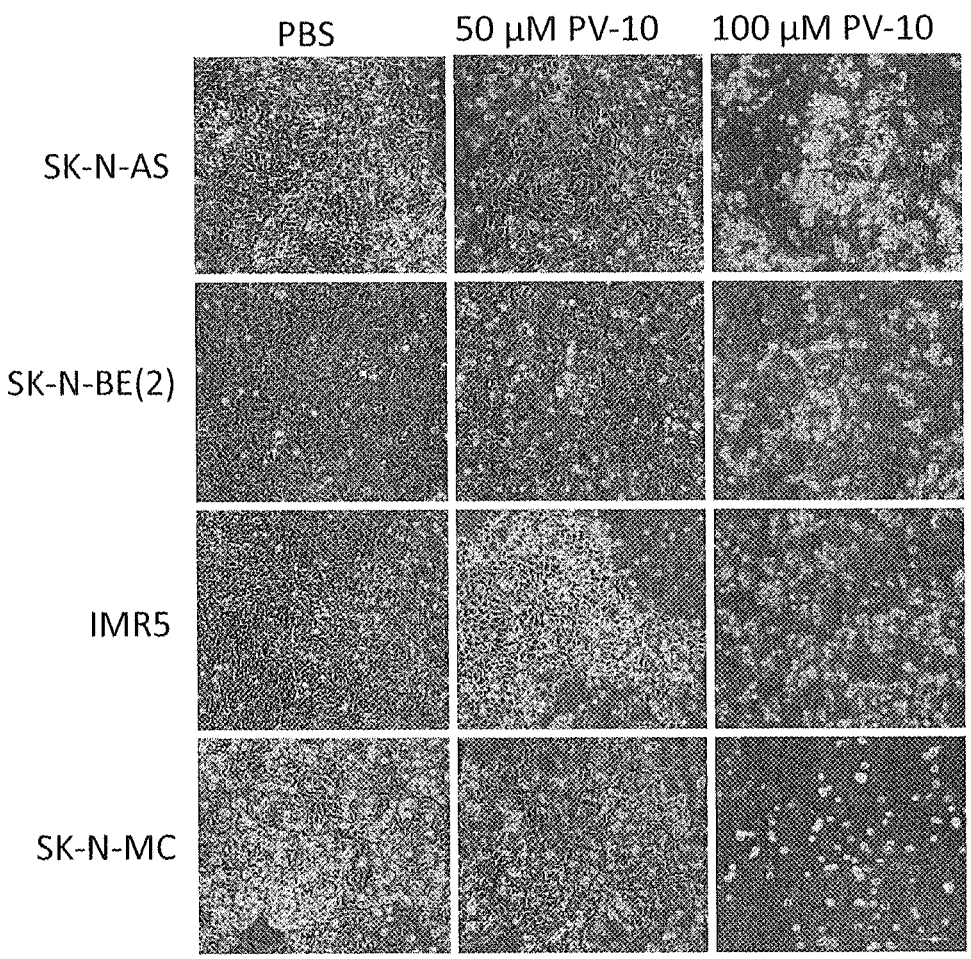
FIGS. 2A and 2B, are photomicrographs showing that PV-10 is cytotoxic to neuroblastoma cell lines.

Cells were treated with either PBS (vehicle control), 50 µM or 100 µM PV-10 for 96 hours and observed by phase-contrast light microscopy (FIG. 2A). Cells treated with PBS grew to confluency. Cells treated with 50 µM PV-10 did not grow to confluency but few dead cells were observed.

By contrast, few cells remained attached to the plate following treatment with 100 µM PV-10, indicating that 100 µM PV-10 was cytotoxic to all cell lines. However, the different cell lines appeared to have different sensitivities to PV-10, with SK-N-AS cells being most resistant to treatment and SK-N-MC being most sensitive to treatment.

Neuroblastoma Cell Lines Display Different Sensitivities to PV-10

Figure 2B:
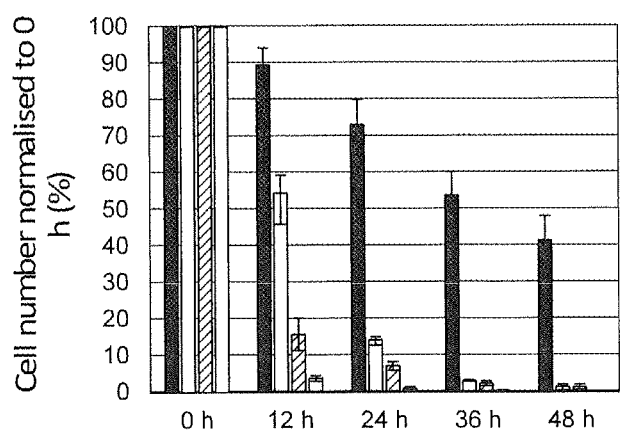

The different sensitivities of the four cell lines (SK-N-AS, SK-N-BE(2), IMR5 and SK-N-MC) to PV-10 were investigated using time-lapse video microscopy to quantify the percentage of cells attached to the plate following 12, 24, 36 and 48 hours of treatment with 100 µM PV-10. The number of cells attached post-treatment was normalized to cell number at zero hours (FIG. 2B).

SK-N-AS cells were most resistant to treatment, at 12 hours 89% and at 48 hours 41% of cells were attached. SK-N-MC cells were most sensitive to treatment, at 12 hours 3.5% and at 48 hours 0% of cells were attached. IMR5 cells were more sensitive to treatment at 12 and 24 hours (16 and 7% of cells attached respectively) by comparison to SK-N-BE(2) cells (54 and 14% of cells attached respectively), but by 36 hours a similar percentage of cells were attached for both cell lines (3% of SK-N-BE(2) and 2% of IMR5 cells).

These data showed that at early times post-treatment, SK-N-MC cells were most sensitive to treatment, IMR5 were more sensitive to treatment than SK-N-BE(2) cells and that SK-N-AS cells were most resistant to treatment.

Treatment with PV-10 Disrupts Lysosomes

Previously, PV-10 had been shown to induce loss of lysosome integrity [6]. SK-N-AS, SK-N-BE(2) and IMR5 cells were therefore treated with either PBS (vehicle control) or 100 µM PV-10 for 16 hours. Live cells were stained with the nucleic acid stain Hoechst 33342 and LysoTracker® Green DND-26 that concentrates and fluoresces in acidic organelles, and the cells were observed by fluorescence microscopy (FIG. 3).

In PBS-treated cells and SK-N-AS PV-10-treated cells, lysosomes were visible as specific foci. However, in PV-10 treated SK-N-BE(2) and IMR5 cells, those foci were no longer visible.

PV-10 Treatment Increases the Percentage of IMR5 Cells in G1 Phase of the Cell Cycle The effect of PV-10 upon the cell cycle by flow cytometry was analyzed (FIGS. 4A-4D) to further determine target modulation of PV-10. The most resistant (SK-N-AS) and most sensitive (IMR5) neuroblastoma cell lines were treated with either PBS (vehicle control), 50 or 100 µM PV-10 for either 16 or 24 hours.

PV-10 had no effect on the cell cycle of SK-N-AS cells. By contrast, 100 µM PV-10 increased the percentage of IMR5 cells in G1 phase. At 16 hours, the percentage of IMR5 cells in G1 phase post-treatment with 100 µM PV-10 increased by 28% when compared to cells treated with PBS. Similarly, at 24 hours, there was a 30% increase in cells in G1 phase post-treatment with 100 µM PV-10, by comparison to un-treated cells.

Treatment with PV-10 Induces Apoptosis

Western blot analysis was then performed to investigate if PV-10 treated cells were undergoing apoptosis. SK-N-AS, SK-N-BE(2), IMR5 and SK-N-MC cells were treated with either PBS (vehicle control), 75 or 100 µM PV-10 for 24 hours. Total cell extracts were analyzed by western blotting to detect levels of total and cleaved poly-ADP ribose (PARP), total and cleaved caspase 3, total and cleaved caspase 7, and actin (loading control) (FIG. 4E).

PV-10 treatment showed a concentration-dependent cleavage of PARP. Treatment with 100 µM PV-10 induced PARP cleavage in all cell lines, with lower total protein and total PARP levels in SK-N-MC cells (the cell line most sensitive to PV-10). SK-N-AS and SK-N-BE(2) cells treated with 75 µM PV-10 showed less PARP cleavage than cells treated with 100 µM PV-10, whereas IMR5 cells had similar levels of PARP cleavage when treated with 75 and 100 µM PV-10. More total PARP was present in SK-N-MC cells treated with 75 µM PV-10 by comparison to cells treated with 100 µM.

Activation of caspases 3, 7 and 9 was dependent on PV-10 concentration and cell line. Cleaved caspase 3 was present in IMR5 cells treated with 100 μM PV-10. Levels of total caspase 7 were lower in SK-N-BE(2) cells.

IMR5 and SK-N-MC cells were treated with both 75 and 100 μM PV-10 and cleaved caspase 7 was detected in 100 μM PV-10 treated SK-N-AS and SK-N-BE(2) cells and 75 and 100 μM PV-10 treated IMR5 cells. Levels of total caspase 9 were lower in 75 and 100 μM PV-10 treated SK-N-BE(2) cells and cleaved caspase 9 was detected in 75 and 100 μM PV-10 treated IMR5 cells. These data indicated that PV-10 was inducing cell death by apoptosis.

PV-10 is Synergistic with Different Anti-Cancer Agents

To determine which commonly used small molecule systemic anti-cancer medications could be combined with PV-10 to enhance cytotoxicity, neuroblastoma cell lines SK-N-AS, SK-N-BE(2) and IMR5, neuroepithelioma cell line SK-N-MC and the normal fibroblast cell line BJ were first screened against a panel of seven conventional chemotherapy agents, having different mechanisms of action (FIGS. 5A-5E). All agents were screened at 0.1 μM, alone and in combination with a sub-cytotoxic concentration of 50 μM PV-10. Cell viability was determined using alamar blue® assay, 96 hours post-treatment.

Based on these results, the agents that showed the largest increase in cytotoxicity when combined, and which had a smaller effect on BJ cells, were selected for further study to determine combination indices (CI) and synergy [18]. Agents evaluated for CI studies in SK-N-AS, SK-N-BE(2), IMR5 and SK-N-MC cells were doxorubicin, etoposide and vincristine.

Table 3, below, provides combination indices for neuroblastoma cell lines (SK-N-AS, SK-N-BE(2) and IMR5) and the neuroepithelioma cell line SK-N-MC treated with either doxorubicin, etoposide or vincristine either alone or in combination with 50 μM PV-10 for 96 hours.

TABLE 3

| Cell Line | Doxorubicin | Etoposide | Vincristine |
|---|---|---|---|
| SK-N-AS | 0.77 | 0.17 | 0.35 |
| SK-N-BE(2) | 0.72 | 0.66 | 0.1 |
| IMR5 | 0.38 | 0.65 | 0.2 |
| SK-N-MC | 0.42 | 0.58 | 0.43 |

All agents demonstrated synergism with 50 μM PV-10 in each of the cell lines assayed. As is seen, CI values ranged from 0.42-0.77 for doxorubicin, 0.17-0.66 for etoposide and 0.1-0.43 for vincristine.

PV-10 Induces Radiosensitivity in Neuroblastoma Cell Lines

In addition to commonly used chemotherapies, whether PV-10 enhanced the effect of treatment with ionizing radiation (IR) in SK-N-AS (FIG. 6A) and IMR5 (FIG. 6B) cells was investigated. Cells were pre-treated for 4 hours with either PBS (vehicle control) or 50 μM PV-10 and then irradiated with either 0.5, 1 or 2 Gray (Gy). Cell viability was measured by alamar blue® 96 hours after initial treatment.

Pre-treatment with 50 μM PV-10 enhanced the effect of IR in both SK-N-AS and IMR5 cells. For SK-N-AS cells, cell viability decreased by 54.8%, 58.7% and 60% when cells were pre-treated with PV-10 for 4 hours prior to irradiation with either 0.5 Gy, 1 Gy or 2 Gy, respectively. For IMR5 cells, cell viability decreased by 24%, 21% and 13% when cells were pre-treated with PV-10 for 4 hours prior to irradiation with either 0.5 Gy, 1 Gy or 2 Gy, respectively.

PV-10 Induces Tumor Regression In Vivo

To determine if PV-10 is also active in vivo, we characterised the effect of PV-10 intratumoral injection on subcutaneous SK-N-AS and IMR tumors in CB17 SCID mice. Tumors were injected once with either 25 or 50 μl PV-10 [8] and monitored daily.

IMR5 tumors were very sensitive to treatment with PV-10 (FIGS. 7A and 7B). For control tumors, tumor size increased from 25.6 mm$^2$ six days post-treatment to 172.9 mm$^2$ 23 days post-treatment. By comparison, tumors treated with 25 μl PV-10 increased from 26.6 mm$^2$ to 41.2 mm$^2$ and tumors treated with 50 μl PV-10 increased from 27.9 mm$^2$ to 47.3 mm$^2$. Tumor growth was also quantified using a Xenogen IVIS® 200 system that measured bioluminescent signal emitted from tumors, following intraperitoneal injection of D-Luciferin.

Tumor size decreased following treatment with 25 and 50 μl PV-10 and remained low 17 days post-treatment. Treatment with PV-10 also increased survival, in a dose-dependent manner (FIG. 7C).

Control treated mice had a median survival of 25.5 days, whereas 25 μl PV-10 treated mice survived a median of 41.5 days and 50 μl PV-10 treated mice survived a median of 76 days. Additionally, two of the mice treated with 50 μl PV-10 underwent complete tumor regression and remained tumor free for 120 days after treatment.

SK-N-AS tumors also responded to treatment with PV-10 (FIGS. 7D and 7E). For control tumors, tumor size increased from 28.9 mm$^2$ six days post-treatment to 179.3 mm$^2$ 18 days post-treatment. By comparison, tumors treated with 25 μl PV-10 increased from 25.3 mm$^2$ to 92.1 mm$^2$ and tumors treated with 50 μl PV-10 increased from 29.3 mm$^2$ to 57.5 mm$^2$. When measured using the Xenogen IVIS® 200 system tumor size decreased following treatment with 25 and 50 μl PV-10 and remained lower than control treated tumors 15 days post-treatment.

Treatment with PV-10 also increased survival (FIG. 7F). Control treated mice had a median survival of 29 days, whereas 25 μl PV-10 treated mice survived a median of 37 days and 50 μl PV-10 treated mice survived a median of 36 days. Additionally, one mouse treated with 50 μl PV-10 underwent complete tumor regression and remained tumor free for 80 days following treatment.

Discussion

The overall survival rate for children with pediatric solid tumors is lower than for children with hematological malignancies [1]. For children with relapsed or metastatic Ewing sarcoma, neuroblastoma, osteosarcoma and rhabdomyosarcoma the overall survival rate is less than 30% [1].

Of these cancers, neuroblastoma is the most common and is a leading cause of death in children aged 1-4 years [2]. Given the poor survival rates of patients with pediatric solid tumors, and the morbidities associated with the intensive treatment regimens administered to high-risk and relapsed patients, there is an urgent need to develop novel therapeutic approaches and early phase clinical trials for patients with these cancers.

PV-10 is a sterile 10% solution of Rose Bengal (RB, 4,5,6,7-tetrachloro-2',4',5',7'-tetraiodofluorescein disodium) in 0.9% saline, that induces cell death in a range of adult cancers, but has not previously been examined for use on pediatric cancers [7-11]. As PV-10 induces cell death in different adult cancers and has been assessed in several clinical trials [10, 12, 14, 15, 16], the effects of PV-10 on different pediatric solid tumor cell lines (Ewing sarcoma, neuroblastoma, osteosarcoma and rhabdomyosarcoma) were investigated.

PV-10 decreased cell viability in pediatric solid tumor cell lines in a concentration-dependent manner. As expected, normal fibroblast cell lines and a primary bone marrow sample were less sensitive to PV-10. These data are similar to previously published data on adult cancers [7, 9, 11] and indicate that PV-10 could be an effective treatment for multiple pediatric solid tumors.

To characterise the target modulation of PV-10, these studies focused on neuroblastoma, the most common of the extra-cranial solid malignancies found in children, and the closely related neuroepithelioma. By phase-contrast microscopy, PV-10 was found to be cytotoxic to neuroblastoma cells and consistent with $IC_{50}$ values, SK-N-AS cells were identified as most resistant and SK-N-MC most sensitive to PV-10 treatment. These findings were verified by time-lapse video microscopy that again showed that SK-N-AS cells were most resistant to treatment and SK-N-MC were most sensitive.

Additionally, IMR5 cells were found to be more sensitive to treatment than SK-N-BE(2) cells at 12 and 24 hours, although by 36 hours few cells of either type remained. Despite the differences in sensitivity to 100 μM PV-10 at early times, this concentration was still cytotoxic to most SK-N-AS cells at 96 hours and increasing the dose to 200 μM further increased SK-N-AS cell death. These data suggest that PV-10 could be an effective treatment for all neuroblastomas, although doses may need to be higher for some sub-types.

The different sensitivities to PV-10 are likely due to the different genetic backgrounds of the cell lines as well as the different histories of the tumors (different patient treatments and primary vs relapsed) from which the cell lines were isolated. Neuroblastoma is a genetically heterogeneous disease and the different cell lines were chosen to reflect that heterogeneity.

The most common oncogenic drivers in neuroblastoma are MYCN amplification that is seen in approximately 25% of patients, anaplastic lymphoma kinase (ALK) mutation and amplification that is seen in approximately 10-15% of patients and mutations in TP53 acquired at relapse [2]. Using the Catalogue of Somatic Mutations in Cancer (COSMIC) Cell Lines Project [20], it was determined that: SK-N-AS cells had mutations in NRAS and FLT3; a clone of SK-N-BE(2) had overexpressed ALK, AKT and MYCN along with a homozygous mutation of TP53; IMR5 cells exhibited over expression of AKT and MYCN with a homozygous mutation of mTOR; and a clone of SK-N-MC exhibited over expression of MYCN and a heterozygous mutation of TP53. Additionally, SK-N-AS, SK-N-BE(2) and SK-N-MC cell lines were all derived from metastatic tumors with different treatment histories, whereas the IMR5 cell line was derived from a primary tumor.

It has previously been shown that PV-10 acts by disrupting lysosomes, leading to cell death [6]. The disruption of lysosomes specifically affects cancer cell survival because cancer cells have an altered metabolism and can depend on lysosomes for the recycling of nutrients and removal of the products of rapid growth and division, such as aggregated proteins and damaged organelles [21]. Furthermore, the disruption of lysosomes releases cathepsin proteases that can lead to induction of necrosis or apoptosis [21].

To investigate the effect of PV-10 on lysosomes in neuroblastoma, cells stained with LysoTracker® Green DND-26, which concentrates and fluoresces in acidic organelles, were observed. Similar to previous results, lysosomes were found to appear as distinct foci in PBS-treated cells but were absent in SK-N-BE(2) and IMR5 cells treated with PV-10. Interestingly, in the more resistant SK-N-AS cells, lysosomes were not disrupted and appeared as distinct foci even after treatment.

Treatment with 100 μM PV-10 induced G1-phase cell cycle arrest in IMR5, but not SK-N-AS cells, and induced apoptosis in a dose- and cell line-dependent manner. It has previously been shown that in adult cancers, PV-10 induces cell death by either apoptosis or necrosis [7, 9, 11, 14]. In the study where cells were found to die by necrosis, PV-10 induced a G2/M cell cycle arrest prior to cell death [7], suggesting that PV-10 may have different mechanisms of action in cell lines from different cancers.

Although treatment with single agent PV-10 has demonstrated efficacy in clinical trials and pre-clinical studies with adult tumors, high-risk neuroblastoma patients are treated with multiple chemotherapies and radiation following relapse [2]. The potential use of PV-10 in combined treatment regimens with commonly used chemotherapeutic agents was therefore investigated.

Following initial screens, a sub-cytotoxic dose of PV-10 (50 μM) was found to be synergistic with doxorubicin, etoposide and vincristine in all cell lines studied. Additionally, pre-treatment with PV-10 before irradiation improved the efficacy of radiation treatment for both SK-N-AS and IMR5 cells. These data are consistent with previous data where, in a Phase-II clinical trial, pre-treatment of melanoma patients with PV-10 followed by radiotherapy, induced tumor regression without a large increase in cytotoxicity [13]. These results indicate that PV-10 can be effectively combined with different commonly used treatments, to benefit high-risk patients with relapsed neuroblastoma.

Having identified that PV-10 was cytotoxic to pediatric solid tumor cell lines in vitro, the activity of PV-10 in vivo was examined using subcutaneous neuroblastoma xenografts in mice. It was found that pharmacologically relevant doses [12, 13, 16] of PV-10 induced tumor regression and increased survival in a dose- and tumor-dependent manner. Intralesional injection of 25 and 50 μl PV-10 induced early tumor regression, with 50 μl PV-10 increasing overall survival in mice with either SK-N-AS or IMR5 tumors. These data are similar to those from previous studies using animal models, where intratumoral injection of PV-10 induced regression of subcutaneous syngeneic colon tumors [7], syngeneic subcutaneous breast tumors and melanoma [14, 8].

In summary, the present studies provide preclinical proof-of-concept data on the efficacy of PV-10 in successfully treating pediatric solid tumors (Ewing sarcoma, neuroblastoma, osteosarcoma, and rhabdomyosarcoma). By focusing on neuroblastoma, it is found that PV-10 acts by disrupting lysosomes, arresting cells at G1-phase of the cell cycle and inducing apoptosis. Several commonly used treatments have been identified with which PV-10 shows synergistic activity. Furthermore, the efficacy of PV-10 treatments in vivo has been validated using neuroblastoma xenograft mouse studies.

The findings carried out in representative cell lines and in in vivo immunocompromised mice provide evidence for direct cytotoxic potential as well as mechanisms by which this agent can induce target modulatory effects in cancer cells. Agents that can be combined to generate treatment synergy have also been identified, providing the framework for the formulation of early phase clinical trials. This in addition to the expected immune stimulatory effect described previously, providing support for a potential approach where a PV-10 backbone regimen can be combined with agents such as immune check point inhibitors to further enhance its activity in patients with relapsed or refractory pediatric solid tumors.

Materials and Methods

Cell Lines and Tissue Culture

Cell lines (SK-N-AS, SK-N-BE(2), IMR5, LAN1, SK-N-MC, SK-N-SH, SHEP, BJ, BJ hTERT, WI38, WI38 hTERT, Hs68 hTERT, RD, RH30, 143B, HOS, SK-ES and SK-PN-DW) were cultured in Dulbecco's Modified Eagle Medium (DMEM) (Gibco, ON, Canada) supplemented with 5% (v/v) heat inactivated fetal bovine serum (FBS) (Gibco), 100 units/ml penicillin and 100 units/ml streptomycin (Gibco). Cell cultures were maintained at 37° C. in a humidified incubator with 5% $CO_2$. The primary bone marrow sample was obtained after local Research Ethics Board (REB) approval and written informed consent (Ethics ID #17184). Lymphocytes were isolated from the bone marrow sample by density gradient centrifugation using Ficoll-Paque Plus (GE Healthcare Life Sciences, ON, Canada), as described previously [17].

Materials and Reagents

PV-10 (10% solution of Rose Bengal disodium in 0.9% saline) was provided by Provectus Biopharmaceuticals Inc. (Knoxville, Tenn., USA) and stored in the dark at room temperature. Stock solutions of doxorubicin, etoposide, vincristine, cisplatin, pegasparaginase, irinotecan and cytarabine were obtained from the Alberta Children's Hospital Pharmacy (Calgary, AB, Canada) and stored at room temperature in the dark. For subsequent studies, the drugs were diluted in DMEM plus supplements to the appropriate concentrations.

Cytotoxicity Assays

Cells were seeded in 96-well plates (Greiner Bio-One, NC, USA) at $5 \times 10^3$ per well in 100 µl DMEM and cultured for 24 hours. PV-10 alone or phosphate buffered saline (PBS; 137 mM NaCl, 2.7 mM KCl, 10 mM $Na_2HPO_4$, 1.8 mM $KH_2PO_4$, pH 7.25) (vehicle control) were diluted in DMEM and a 100 µl treatment was added to each well. All treatments were run in triplicate at final concentrations ranging from 3.125 to 400 µM.

Plates were cultured for 96 hours. Wells were washed twice with PBS, 200 µl fresh DMEM was added to each well and cell viability was evaluated using the alamar blue® (Invitrogen, ON, Canada) cytotoxicity assay as per manufacturer's instructions. One-half maximal inhibitory concentrations ($IC_{50}$) were determined using CompuSyn software (ComboSyn Inc.).

Light Microscopy

Cells were seeded in 6-well plates (Corning Inc., NY, USA) at $2 \times 10^5$ per well and cultured for 24 hours. Cells were treated with either PBS (vehicle control) or PV-10 and cultured for 96 hours. Phase-contrast images were captured on a Zeiss Axiovert 200M microscope with a Zeiss Axio-Cam MRm Rev.3 FireWire camera using Zeiss AxioVision Se64 software. Images were processed using Adobe Photoshop (Adobe Creative Cloud 2017).

Time-Lapse Video Microscopy

Cells were seeded in 96-well plates (Greiner Bio-One) at $5 \times 10^3$ per well and cultured for 24 hours. Cells were treated with either PBS (vehicle control) or PV-10. Three images per well were captured every 30 minutes for 48 hours using an IncuCyte® Zoom microscope and IncuCyte® Zoom software (Essen BioScience, MI, USA) located in a humidified incubator with 5% $CO_2$ at 37° C. Cell numbers in each well were counted using Image) software and normalized to cell number at zero hours. At least 350 cells were counted per treatment per experiment.

Lysosome Detection and Fluorescence Microscopy

Cells were seeded onto sterile coverslips in 6-well plates (Corning) at $2 \times 10^5$/well for not treated cells and $6 \times 10^5$/well for treated cells in 6-well plates (Corning) and cultured for 24 hours. Cells were treated with either PBS (vehicle control) or PV-10 for 16 hours. Wells were washed twice with PBS and 2 ml DMEM containing 2.5 µg/ml Hoechst 33342 stain (Invitrogen) was added to each well. Cells were incubated at 37° C. for ten minutes and then Lysotracker® Green DND-26 (Invitrogen) was added to the media at 500 nM final concentration. Cells were incubated at 37° C. for 15 minutes, coverslips were mounted onto glass slides at time of imaging and images were captured on a Zeiss Axiovert 200M microscope with a Zeiss AxioCam MRm Rev.3 FireWire camera using Zeiss AxioVision Se64 software. Images were processed using Adobe Photoshop (Adobe Creative Cloud 2018).

Flow Cytometry

To analyse cell cycle alterations, cells were seeded in 100 mm dishes (Corning), so that a minimum of $2 \times 10^6$ cells could be collected post-treatment. Cells were cultured for 24 hours, treated with either PBS (vehicle control) or PV-10 and cultured for either 16 or 24 hours. Cells were collected by trypsinization, washed with PBS, filtered through a 40 µm nylon cell strainer (Falcon, Corning, NY, USA), counted using trypan blue staining using a haemocytometer, resuspended in 0.9% (w/v) sterile NaCl and fixed in ice-cold 90% (v/v) ethanol. Samples were incubated at room temperature for 30 minutes then stored at −20° C.

For analysis, samples were centrifuged at 1400 rpm for five minutes at 4° C. and washed twice with ice cold PBS. Cells were then incubated at 37° C. for 20 minutes in 300 µl labelling buffer: 10 µg/ml DAPI (Sigma, ON, Canada), 200 µg/ml RNase A (Sigma) in 0.1% Triton X-100 in PBS. Samples were run on a BD Bioscience LSR II cytometer using Diva 6.1.3 software (BD Bioscience). Results were analyzed using ModFitLT™ 3.3 software (Verity Software House).

Preparation of Cellular Extracts

Cells were seeded at $1 \times 10^6$ in 100 mm dishes (Corning) and cultured for 24 hours. Cells were then treated with either PBS (vehicle control) or PV-10 and cultured for 24 hours. Medium was collected from cell cultures, cells were washed with PBS and collected following trypsinisation. Cells were washed in ice cold PBS and centrifuged at 1200 rpm at 4° C. for five minutes. The supernatant was removed, and the pellet was resuspended in radioimmunoprecipitation assay (RIPA) buffer (50 mM Tris-HCl (pH 8), 150 mM NaCl, 1% (v/v) NP-40, 0.5% (w/v) sodium deoxycholate, 0.1% (w/v) sodium dodecyl sulfate (SDS)) supplemented with 1% (v/v) phosphatase inhibitor (Sigma) and 1% (v/v) protease inhibitor (Sigma). Samples were transferred to 1.5 ml tubes, incubated on ice for ten minutes, vortexed and centrifuged at 12,000 rpm for ten minutes. Supernatants were collected as whole cell lysates and either used immediately or stored at −20° C.

Western Blotting

Western blotting was carried cut as described previously [17]. Briefly, proteins were transferred to nitrocellulose membrane using a Trans-Blot® Turbo™ Transfer System (BioRad, QC, Canada), transfer was confirmed using Ponceau S stain (0.1% (w/v) in 5% (v/v) acetic acid) and membranes were blocked in 5% skim milk in Tris-buffered saline with 0.1% (v/v) Tween®-20 (TBS-T; 50 mM Tris-HCl, pH 7.5, 150 mM NaCl, 0.1% (v/v) Tween®-20) at room temperature for two hours. Membranes were then incubated overnight (about 18 hours) at 4° C. with the following primary antibodies diluted in 5% (w/v) skim milk in TBS-T: Anti-PARP (1:3000, Cell Signaling, 9542S), anti-caspase 3 (1:500, Cell Signaling, 9662S), anti-caspase 7 (1:1000, Cell signaling, 9492S), anti-caspase 9 (1:1000, Cell Signaling, 9502S) and anti-β-actin (1:5000, Cell Signaling, 8457L). Membranes were washed three times with TBS-T, incubated with anti-rabbit secondary antibody (1:3000, Cell signaling, 7074S), washed three times with TBS-T, incubated with Western Lightning Plus-ECL reagent (Perkin-Elmer, MA, USA) for two minutes and developed using the chemiluminescence setting on a ChemiDoc MP Imaging System (BioRad).

Combination Screens

Cells were cultured as described for cytotoxicity assays. Test drugs (doxorubicin, etoposide, vincristine, cisplatin, pegasparaginase, irinotecan, cytarabine) were prepared at a final concentration of 0.1 µM in media containing either PBS (vehicle control) or PV10 (50 µM final). Treatments were added to cells in triplicate. Plates were cultured, washed and cell viability analyzed by alamar blue®, as described for cytotoxicity assays.

Combination Studies

Cells were cultured as described for cytotoxicity assays. A dilution series of three test drugs (doxorubicin, etoposide, vincristine) were prepared in DMEM containing either PBS (vehicle control) or PV10 (50 µM final) and added to cells in triplicate. Plates were cultured, washed and cell viability analyzed by alamar blue®, as described for cytotoxicity assays. Combination indices (CI) for $IC_{50}$ of test drug in combination with 50 µM PV-10 were calculated using CompuSyn software (ComboSyn Inc.). CI values were scored according to the following criteria CI<1 indicated synergistic activity, CI=1 indicated additive activity and CI>1 indicated synergistic activity [18].

Radiosensitivity Assays

Cells were seeded at $5 \times 10^4$ in 60 mm dishes (Corning) and incubated for 24 hours and treated with either PBS (vehicle control) or 50 µM PV-10 and incubated at 37° C. for four hours. Cells were irradiated with either 0.5, 1 or 2 Gray (Gy) using a Gammacell® 1000 Elite (MDS Nordion, ON, Canada) and cultured for 92 hours. Treatments were run in triplicate. Dishes were washed twice with PBS and cell viability was analyzed by alamar blue®, as described for cytotoxicity assays.

In Vivo Xenograft Models

All animal procedures were carried out in accordance with the guidelines of the Canadian Council on Animal Care and the NIH guidelines on the care and use of laboratory animals. All protocols were reviewed and approved by the Animal Care Committee of the University of Calgary (Protocol approval number: AC16-0243).

IMR5-mCherryFluc and SK-N-AS-mCherryFluc cells were used in the animal studies. These cell lines stably expressed enhanced firefly luciferase and mCherry on a self-inactivating lentiviral vector encoding the internal U3 region from murine stem cell virus (mscv), enhanced firefly luciferase (effLuc), the internal ribosomal entry site (IRES) element from encephalomyocarditis virus (emcv), and mCherry.

Six to eight-week-old female CB17 SCID mice (Charles River Laboratories, QC, Canada) were subcutaneously injected in the right flank with $2.5 \times 10^6$ cells (SK-N-ASmCherryFluc or IMR5mCherryFluc) suspended in 0.1 ml Matrigel® Matrix (Fischer Scientific, ON, Canada) (Day zero). Seven days after tumor injection, animals with detectable tumor growth of at least 5×5 mm were randomised into treatment groups. The groups were treated with either 50 µl PBS (vehicle control), 50 µl PV-10 or 25 µl PV-10 by intratumoral (intralesional) injection, according to a previously established protocol [8]. Animals were monitored daily and tumor areas were determined with a Vernier caliper. When tumors reached the defined end-point of 15×15 mm, mice were euthanized. Animals that remained tumor-free were kept for 120 days post-treatment.

Tumor growth was also monitored using the Xenogen IVIS® 200 system (Xenogen Corporation, CA, USA). Mice were imaged to document bioluminescent signal emitted from tumors, following intraperitoneal injection of D-Luciferin (Gold Biotechnology, MO, USA). Data were analyzed by determining total photon flux emission (photons/s) in the region of interest, as per established methods [19].

CITATIONS

1. Chen X, Pappo A, Dyer M A. Pediatric solid tumor genomics and developmental pliancy. Oncogene. 2015; 34:5207. doi:10.1038/onc.2014.474.

2. Moreno L, Caron H, Geoerger B, Eggert A, Schleiermacher G, Brock P et al. Accelerating drug development for neuroblastoma—New Drug Development Strategy: an Innovative Therapies for Children with Cancer, European Network for Cancer Research in Children and Adolescents and International Society of Paediatric Oncology Europe Neuroblastoma project. Expert opinion on drug discovery. 2017; 12(8):801-11. doi:10.1080/17460441.2017.1340269.

3. Cheung N-K V, Dyer M A. Neuroblastoma: Developmental Biology, Cancer Genomics, and Immunotherapy. Nature reviews Cancer. 2013; 13(6):397-411. doi:10.1038/nrc3526.

4. Park J R, Bagatell R, London W B, Maris J M, Cohn S L, Mattay K K et al. Children's Oncology Group's 2013 blueprint for research: neuroblastoma. Pediatric blood & cancer. 2013; 60(6):985-93. doi:10.1002/pbc.24433.

5. Yvart J, Moati F, Alvarez F. Odievre M. Degrez A. $^{131}$I Rose Bengal: Its Use in the Evaluation of Infantile Jaundice. European Journal of Nuclear Medicine. 1981; 6:355-359.

6. Wachter, E., Dees, C., Harkins, J., Fisher, W., Scott, T. 2002. Functional imaging of photosensitizers using multiphoton microscopy. Proceedings of SPIE, Multiphoton Microscopy in the Biomedical Sciences II, Periasamy, A. and So, P. T. C. (eds), Bellingham, Wash.: 4620: 143-147.

7. Qin J, Kunda N, Qiao G, Calata J F, Pardiwala K, Prabhakar B S et al. Colon cancer cell treatment with Rose Bengal generates a protective immune response via immunogenic cell death. Cell Death &Amp; Disease. 2017; 8:e2584. doi:10.1038/cddis.2016.473

8. Toomey P, Kodumudi K, Weber A, Kuhn L, Moore E, Sarnaik A A et al. Intralesional Injection of Rose Bengal Induces a Systemic Tumor-Specific Immune Response in Murine Models of Melanoma and Breast Cancer. PLoS ONE. 2013; 8(7):e68561. doi:10.1371/journal.pone.0068561.

9. Koevary S B. Selective toxicity of Rose Bengal to ovarian cancer cells in vitro. International journal of physiology, pathophysiology and pharmacology. 2012; 4(2):99-107.

10. Thompson J F, Hersey P, Wachter E. Chemoablation of metastatic melanoma using intralesional Rose Bengal. Melanoma research. 2008; 18(6):405-11. doi:10.1097/CMR.0b013e32831328c7.

11. Zamani Taghizadeh Rabe S, Mousavi S H, Tabasi N, Rastin M, Zamani Taghizadeh Rabe S, Siadat Z et al. Rose Bengal suppresses gastric cancer cell proliferation via apoptosis and inhibits nitric oxide formation in macrophages.

Journal of immunotoxicology. 2014; 11(4):367-75. doi: 10.3109/1547691x.2013.853715.

12. Thompson J F, Agarwala S S, Smithers B M, Ross M I, Scoggins C R, Coventry B J et al. Phase 2 Study of Intralesional PV-10 in Refractory Metastatic Melanoma. Annals of surgical oncology. 2015; 22(7):2135-42. doi: 10.1245/s10434-014-4169-5.

13. Foote M, Read T, Thomas J, Wagels M, Burmeister B, Smithers B M. Results of a phase II, open-label, non-comparative study of intralesional PV-10 followed by radiotherapy for the treatment of in-transit or metastatic melanoma. Journal of surgical oncology. 2017; 115(7):891-7. doi:10.1002/jso.24580.

14. Liu H, Innamarato P P, Kodumudi K, Weber A, Nemoto S, Robinson J L et al. Intralesional Rose Bengal in melanoma elicits tumor immunity via activation of dendritic cells by the release of high mobility group box 1. Oncotarget. 2016; 7(25):37893-905. doi:10.18632/oncotarget.9247.

15. Lippey J, Bousounis R, Behrenbruch C, McKay B, Spillane J, Henderson M A et al. Intralesional PV-10 for in-transit melanoma-A single-center experience. Journal of surgical oncology. 2016; 114(3):380-4. doi:10.1002/jso.24311.

16. Ross M I. Intralesional therapy with PV-10 (Rose Bengal) for in-transit melanoma. Journal of surgical oncology. 2014; 109(4):314-9. doi:10.1002/jso.23554.

17. Jayanthan A, Ruan Y, Truong T H, Narendran A. Aurora kinases as druggable targets in pediatric leukemia: heterogeneity in target modulation activities and cytotoxicity by diverse novel therapeutic agents. PLoS One. 2014; 9(7):e102741. doi:10.1371/journal.pone.0102741.

18. Chou T-C. Drug Combination Studies and Their Synergy Quantification Using the Chou-Talalay Method. Cancer Research. 2010; 70(2):440.

19. Lun X, Ruan Y, Jayanthan A, Liu D J, Singh A, Trippett T et al. Double-deleted vaccinia virus in virotherapy for refractory and metastatic pediatric solid tumors. Molecular oncology. 2013; 7(5):944-54. doi:10.1016/j.molonc.2013.05.004.

20. Catalogue of Somatic Mutations in Cancer (COSMIC). https://cancer.sanger.ac.uk/cosmic. Accessed 30.10.17.

21. Fennelly C, Amaravadi R K. Lysosomal Biology in Cancer. Methods in molecular biology (Clifton, N.J.). 2017; 1594:293-308. doi:10.1007/978-1-4939-6934-0-19.

The invention claimed is:

1. A method of treating a pediatric cancerous solid tumor selected from one or more of the group consisting of Ewing sarcoma, neuroblastoma, osteosarcoma, neuroepithelioma, and rhabdomyosarcoma in a mammalian subject that comprises intralesionally administering an amount of rose bengal or a pharmaceutically acceptable salt thereof that elicits ablation of tumor cells.

2. The method according to claim 1, wherein the pharmaceutically acceptable salt of rose bengal is rose bengal disodium.

3. The method according to claim 1, wherein said mammal is a human.

4. A method of treating a pediatric cancerous solid tumor selected from one or more of the group consisting of Ewing sarcoma, neuroblastoma, osteosarcoma, neuroepithelioma, and rhabdomyosarcoma in a mammalian subject that comprises (1) intralesionally administering an amount of rose bengal or a pharmaceutically acceptable salt thereof that elicits ablation of tumor cells and (2) administering a tumor-inhibiting effective amount of a systemic anti-cancer medication that provides synergistic cytotoxicity with said rose bengal, said systemic anti-cancer medication being selected from one or more of doxorubicin, etoposide and vincristine.

5. The method according to claim 4, wherein said rose bengal is rose bengal disodium.

6. The method according to claim 4, wherein said intralesional administration of a rose bengal or a pharmaceutically acceptable salt thereof occurs prior to administration of said systemic anti-cancer medication.

7. The method according to claim 4, wherein said intralesional administration of a rose bengal or a pharmaceutically acceptable salt thereof occurs after administration of said systemic anti-cancer medication.

8. The method according to claim 4, wherein said intralesional administration of a rose bengal or a pharmaceutically acceptable salt thereof occurs concurrent with administration of said systemic anti-cancer medication.

9. The method according to claim 4, wherein said mammal is a human.

10. A method of treating a pediatric cancerous solid tumor selected from one or more of the group consisting of Ewing sarcoma, neuroblastoma, osteosarcoma, neuroepithelioma, and rhabdomyosarcoma in a mammalian subject that comprises (1) intralesionally administering an amount of rose bengal or a pharmaceutically acceptable salt thereof that elicits ablation of tumor cells and (2) administering a tumor-inhibiting effective amount of by ionizing radiation.

11. The method according to claim 10, wherein said rose bengal is rose bengal disodium.

12. The method according to claim 10, wherein said mammal is a human.

13. The method according to claim 1 further including the step of administering a tumor-inhibiting effective amount of a small molecule systemic anti-cancer medication selected from the group consisting of doxorubicin, etoposide, vincristine, cisplatin, irinotecan and cytarabine.

* * * * *